(12) United States Patent
Asai

(10) Patent No.: US 12,066,463 B2
(45) Date of Patent: Aug. 20, 2024

(54) INFORMATION PROCESSING APPARATUS, COMPUTER-READABLE MEDIUM, AND INFORMATION PROCESSING METHOD

(71) Applicant: Miyako Asai, Kanagawa (JP)

(72) Inventor: Miyako Asai, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 92 days.

(21) Appl. No.: 17/868,798

(22) Filed: Jul. 20, 2022

(65) Prior Publication Data

US 2023/0034939 A1    Feb. 2, 2023

(30) Foreign Application Priority Data

Jul. 30, 2021 (JP) .................................. 2021-125541

(51) Int. Cl.
*G01R 13/02*    (2006.01)

(52) U.S. Cl.
CPC ........ *G01R 13/029* (2013.01); *G06F 2218/10* (2023.01); *G06F 2218/14* (2023.01)

(58) Field of Classification Search
CPC ............... G01R 13/029; G06F 2218/14; G06F 2218/10
See application file for complete search history.

(56) References Cited

U.S. PATENT DOCUMENTS

| 9,076,457 B1* | 7/2015 | Orler ..................... G11B 27/105 |
| 2010/0194755 A1* | 8/2010 | Foo ......................... G01R 13/02 |
| | | 345/440 |
| 2020/0100695 A1* | 4/2020 | Misaka .................. A61B 5/055 |
| 2020/0230336 A1* | 7/2020 | Angelico ............ A61M 16/024 |
| 2021/0109130 A1* | 4/2021 | Barthel ................ G01R 13/029 |
| 2021/0128002 A1 | 5/2021 | Hirano et al. |
| 2021/0132125 A1 | 5/2021 | Hirano et al. |

FOREIGN PATENT DOCUMENTS

| JP | 2009-118910 | 6/2009 |
| JP | 2011-254944 | 12/2011 |
| JP | 2020-080121 | 5/2020 |
| JP | 2021-069929 | 5/2021 |

* cited by examiner

*Primary Examiner* — Mohamed Charioui
*Assistant Examiner* — Xiuqin Sun
(74) *Attorney, Agent, or Firm* — XSENSUS LLP

(57) ABSTRACT

An information processing apparatus includes an extraction unit, a determination unit, a display control unit, and a display unit. The extraction unit is configured to extract, by predetermined pattern matching, candidate peaks in a certain arbitrary period of time from among at least one or more pieces of waveform data. The determination unit is configured to determine, from among the candidate peaks of the waveform data, a single peak based on a score related to the pattern matching. The display control unit is configured to output display information for displaying a position of the peak. The display unit is configured to display the display information.

6 Claims, 13 Drawing Sheets

INFORMATION PROCESSING APPARATUS, COMPUTER-READABLE MEDIUM, AND INFORMATION PROCESSING METHOD

CROSS-REFERENCE TO RELATED APPLICATIONS

The present application claims priority under 35 U.S.C. §119 to Japanese Patent Application No. 2021-125541, filed on Jul. 30, 2021. The contents of which are incorporated herein by reference in their entirety.

BACKGROUND OF THE INVENTION

1. Field of the Invention

The present invention relates to an information processing apparatus, a computer-readable medium, and an information processing method.

2. Description of the Related Art

Conventionally, in preoperative evaluation for epilepsy using magnetoencephalography in clinical practice, a current source (dipole) that generates a magnetic field that is measured on a scalp is estimated to evaluate locality of an epilepsy lesion. To estimate the dipole, it is necessary to narrow down a time (start part) at which characteristic waveform information (Interictal Epileptiform Discharge (IED)) is generated and a sensor in which the waveform information appears from time series of a plurality of sensors.

In the present circumstances, a doctor manually searches for an IED and determines a start part; however, an amount of magnetoencephalography data is enormous, and therefore, it is difficult to manually and accurately extract a sensor and a time of an IED for each of IEDs. Japanese Unexamined Patent Application Publication No. 2009-118910 discloses a technology of displaying, in real time, a value of peak data of a single output among outputs that are measured by a plurality of magnetic flux sensors and a corresponding channel number on a screen that displays a measurement result, and displaying a reactive site with a strong brain magnetic field that is detected by each of the sensors.

However, according to the conventional technology, there is a problem in that it is difficult to detect a peak time while taking into account data from a plurality of sensors.

SUMMARY OF THE INVENTION

An information processing apparatus includes an extraction unit, a determination unit, a display control unit, and a display unit. The extraction unit is configured to extract, by predetermined pattern matching, candidate peaks in a certain arbitrary period of time from among at least one or more pieces of waveform data. The determination unit is configured to determine, from among the candidate peaks of the waveform data, a single peak based on a score related to the pattern matching. The display control unit is configured to output display information for displaying a position of the peak. The display unit is configured to display the display information.

BRIEF DESCRIPTION OF THE DRAWINGS

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
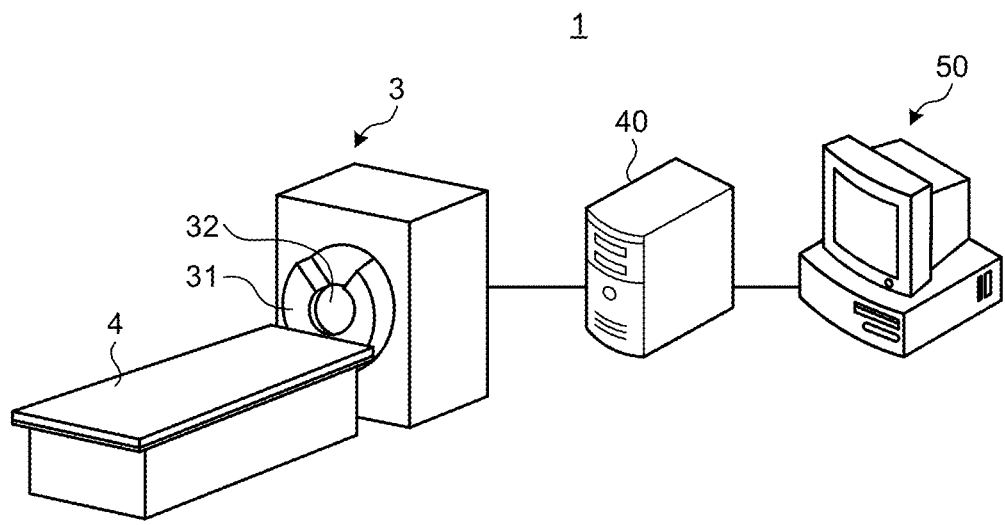
FIG. 1 is a schematic diagram illustrating a configuration of a biological signal measurement system according to a first embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

An embodiment has an object to determine a single peak from among candidate peaks of waveforms that are extracted from time series of a plurality of sensors, to determine a reference point for analysis.

Embodiments of an information processing apparatus, a computer-readable medium, and an information processing method will be described in detail below with reference to the accompanying drawings. The present invention is not limited by the embodiments below, and components in the embodiments described below include one that can easily be thought of by a person skilled in the art, one that is practically identical, and one that is within an equivalent range. Further, within the scope not departing from the gist of the following embodiments, various omission, replacement, and modifications of the components may be made.

First Embodiment

Overview of Biological Signal Measurement System

FIG. 1 is a schematic diagram illustrating a configuration of a biological signal measurement system according to a first embodiment. An overview of a biological signal measurement system 1 according to the present embodiment will be described with reference to FIG. 1.

The biological signal measurement system 1 is a system that measures a plurality of kinds of biological signals (for example, a magnetoencephalography (MEG) signal and an electroencephalography (EEG) signal) of a subject from a specific transmission source (living body site) and displays the biological signals. In the present invention, the biological signals to be measured are not limited to the magnetoencephalography signal and the electroencephalography signal, but may be, for example, an electrical signal that is generated in accordance with activity of a heart (electrical signal that can be expressed by an electrocardiogram) or the like.

The electroencephalography signal is a signal that represents electrical activity of a nerve cell (ion charge flow that occurs in dendrites of a neuron at the time of synaptic transmission) as a voltage value between electrodes. The magnetoencephalography signal is a signal that represents minute electric field variation that occurs due to electrical activity of a brain.

As illustrated in FIG. 1, the biological signal measurement system 1 includes a measurement apparatus 3 that measures one or more biological signals of a subject, a server 40 that records one or more kinds of biological signals measured by the measurement apparatus 3, and an information processing apparatus 50 that is a biological signal display apparatus for analyzing the one or more kinds of biological signals recorded in the server 40. The measurement apparatus 3 is, for example, a magnetoencephalographm that collects a measurement value of a brain's magnetic field or a measurement value at a timing at which a stimulus is applied. While the server 40 and the information processing apparatus 50 are separately illustrated in FIG. 1, at least a part of functions of the server 40 may be incorporated in the information processing apparatus 50, for example.

A purpose of performing measurement using the magnetoencephalogram before epilepsy operation will be described below. For operation of excising a nerve cell that causes an abnormal firing phenomenon as a focus of epilepsy, the measurement using the magnetoencephalogram is performed to identify a position at which a diseased nerve cell is present. By accurately identifying the position with high precision, it is possible to reduce an excised area and improve the quality of life (QOL) of a patient.

In the example illustrated in FIG. 1, the subject (measurement target person) lies down on a measurement table 4 with face up while mounting electrodes (or sensors) for electroencephalography on his/her head, and inserts a head portion in a hollow 32 of a dewar 31 of the measurement apparatus 3. The dewar 31 is a holding container in an extremely low temperature environment using liquid helium, and a large number of magnetic sensors for magnetoencephalography are arranged inside the hollow 32 of the dewar 31. The measurement apparatus 3 collects electroencephalography signals from the electrodes and magnetoencephalography signals from the magnetic sensors, and outputs data (hereinafter, may be referred to as "measurement data") including the collected electroencephalography signals and the collected magnetoencephalography signals to the server 40. The measurement data output to the server 40 is read, displayed, and analyzed by the information processing apparatus 50. In general, the dewar 30 in which the magnetic sensors are incorporated and the measurement table 4 are arranged in a magnetic shielding room, but illustration of the magnetic shielding room is omitted in FIG. 1 for the sake of convenience.

The information processing apparatus 50 is an apparatus that displays waveform data of the magnetoencephalography signals from the plurality of magnetic sensors and waveform data of the electroencephalography signals from the plurality of electrodes on the same time axis in a synchronous manner. Each of the electroencephalography signals is a signal that represents electrical activity of a nerve cell (ion charge flow that occurs in dendrites of a neuron at the time of synaptic transmission) as a voltage value between the electrodes. Each of the magnetoencephalography signals is a signal that represents minute electric field variation that occurs due to electrical activity of a brain. A brain's magnetic field is detected by a superconducting quantum interference device (SQUID) sensor. The electroencephalography signals and the magnetoencephalography signals are examples of "biological signals".

Figure 2:
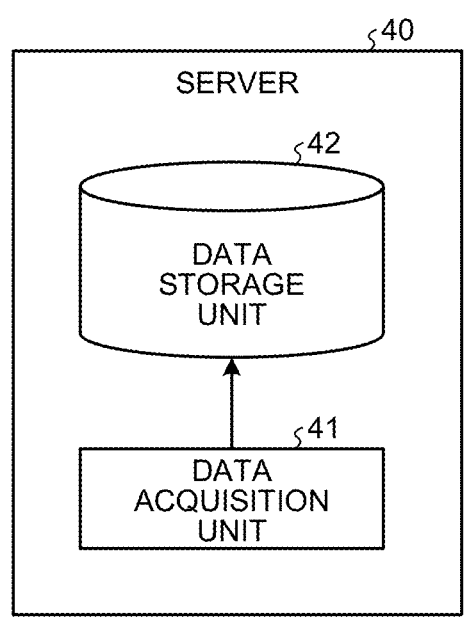
FIG. 2 is a block diagram schematically illustrating a functional configuration of a server.

FIG. 2 is a block diagram schematically illustrating a functional configuration of the server 40. As illustrated in FIG. 2, the server 40 includes a data acquisition unit 41 and a data storage unit 42.

The data acquisition unit 41 periodically acquires measurement data from the measurement apparatus 3. Here, the measurement data is each piece of waveform data measured by the plurality of magnetic sensors of the dewar 31 of the measurement apparatus 3.

The data storage unit 42 stores therein the measurement data acquired from the measurement apparatus 3.

Hardware Configuration of Information Processing Apparatus

Figure 3:
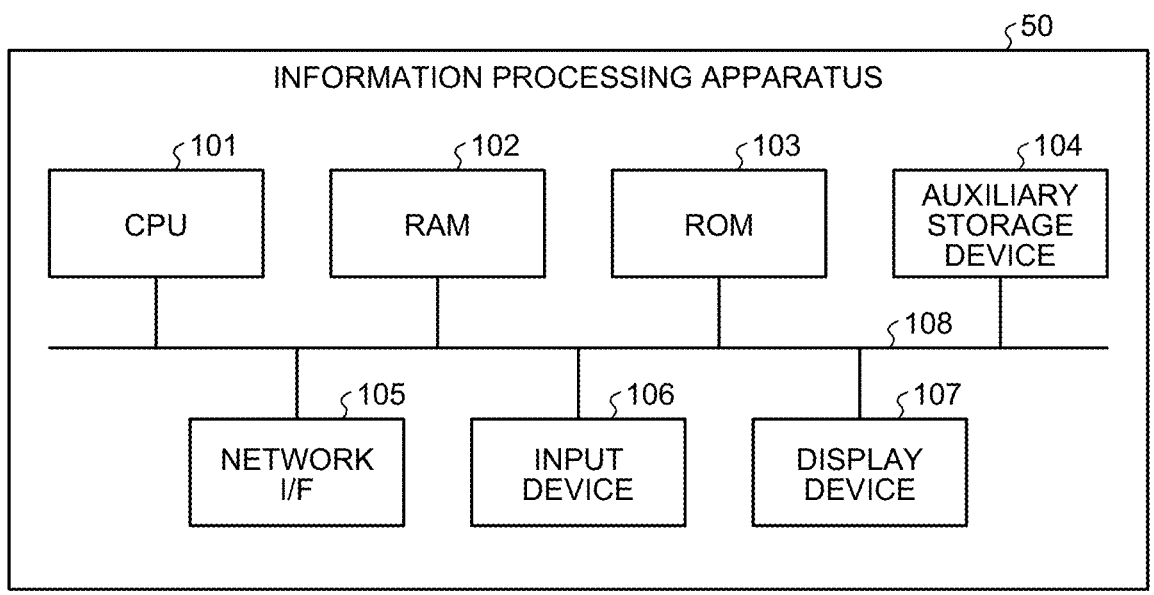
FIG. 3 is a diagram illustrating an example of a hardware configuration of an information processing apparatus.

FIG. 3 is a diagram illustrating an example of a hardware configuration of the information processing apparatus 50. The hardware configuration of the information processing apparatus 50 will be described below with reference to FIG. 3.

As illustrated in FIG. 3, the information processing apparatus 50 includes a central processing unit (CPU) 101, a random access memory (RAM) 102, a read only memory (ROM) 103, an auxiliary storage device 104, a network interface (I/F) 105, an input device 106, and a display device 107, all of which are connected to one another via a bus 108.

The CPU 101 is an arithmetic device that controls entire operation of the information processing apparatus 50 and performs various kinds of information processing. The CPU 101 executes an information display program that is stored in the ROM 103 or the auxiliary storage device 104, and controls operation of displaying a measurement collection screen and an analysis screen.

The RAM 102 is a volatile storage device that is used as a work area for the CPU 101 and stores therein a main control parameter and information. The ROM 103 is a nonvolatile storage device that stores therein basic input-output program or the like. For example, the information display program as described above may be stored in the ROM 103.

The auxiliary storage device 104 is a storage device, such as a hard disk drive (HDD) or a solid state drive (SSD). The auxiliary storage device 104 stores therein, for example, a control program for controlling the operation of the information processing apparatus 50, and various kinds of data, files, and the like that are needed for the operation of the information processing apparatus 50.

The network I/F 105 is a communication interface for performing communication with an apparatus, such as the server 40, on a network. The network I/F 105 is implemented by a network interface card (NIC) or the like that is compliant with transmission control protocol/Internet protocol (TCP/IP), for example.

The input device 106 is a user interface, such as an input function of a touch panel, a keyboard, a mouse, or an operation button, or the like. The display device 107 is a display device for displaying various kinds of information. The display device 107 functions as a display means and is implemented by a display function of the touch panel, a liquid crystal display (LCD), an organic electro-luminescence (EL), or the like, for example. The display device 107 displays the measurement collection screen and the analysis screen, and the screens are updated in accordance with input-output operation that is performed via the input device 106.

Examples of the screens displayed on the display device 107 will be described below.

Figure 4:
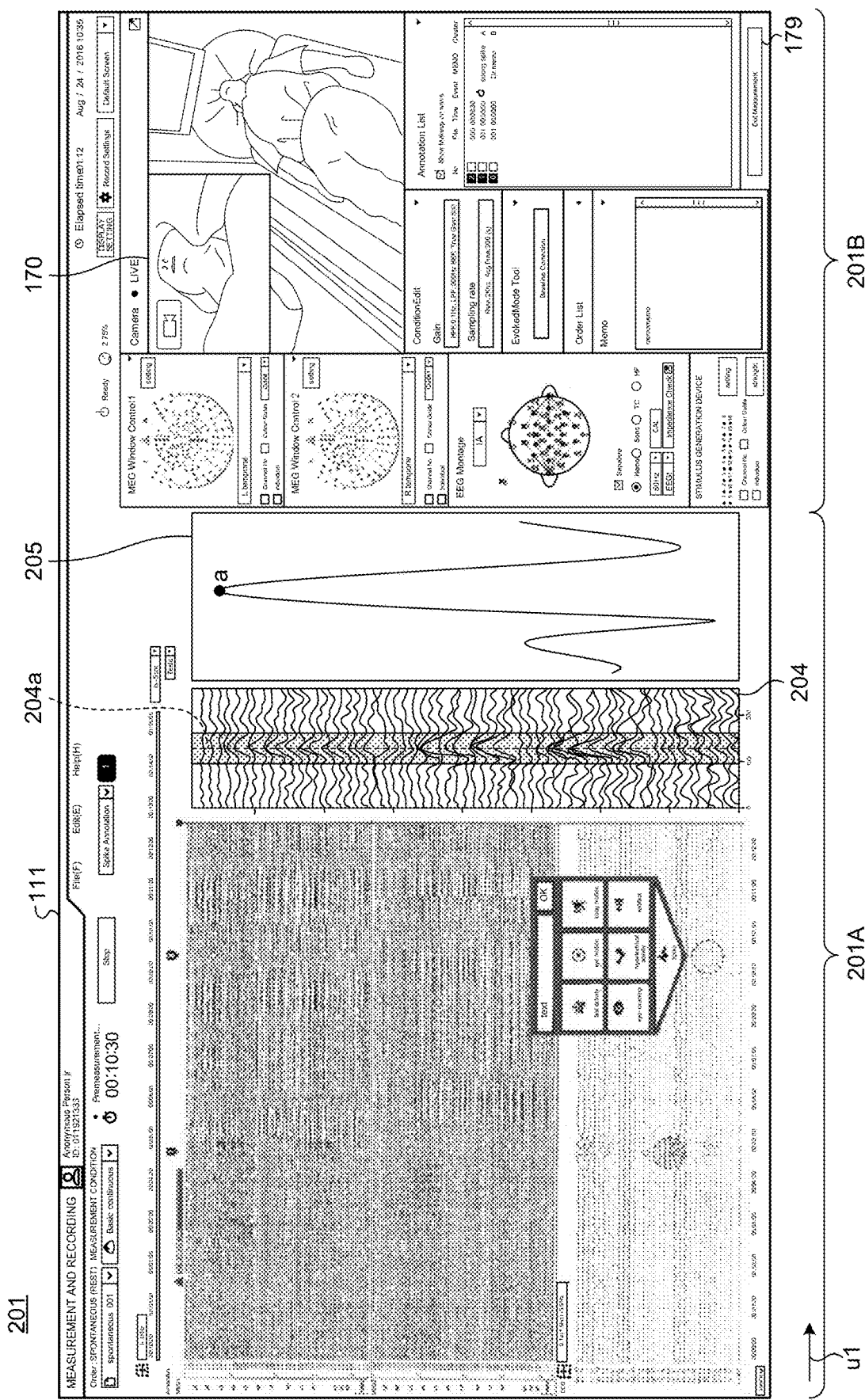
FIG. 4 is a diagram illustrating an example of a measurement recording screen.

FIG. 4 is a diagram illustrating an example of a measurement recording screen. In a measurement recording screen (or may be simply referred to as a "screen") 201 illustrated in FIG. 4, information indicating that the screen is for "measurement recording" is displayed on a tab 111 in the screen 201. The measurement recording screen 201 includes a region 201A for displaying a signal waveform of a biological signal, and a region 201B for displaying monitor information other than the signal waveform. The region 201A for displaying the signal waveform is arranged on the left side in the screen 201 when viewed from a measurer, and the region 201B for displaying the monitor information other than the signal waveform is arranged on the right side in the screen 201 when viewed from the measurer. Movement of a line of sight of the measurer with movement of the waveform that is detected in real time and that is displayed horizontally in a rightward direction (direction u1) from a left edge of the screen 201 efficiently matches movement of a mouse from the region 201A on the left side in the screen 201 to the region 201B on the right side, so that operation efficiency is improved. The "horizontal" described herein indicates an arbitrary line that is parallel to the direction u1 in the screen 201, and the same applies to the description below. Further, in the present specification, when a figure representing the entire screen is referred to, "left", "right", "top", and "bottom" are appropriately used, and the "left", the "right", the "top", and the "bottom" indicate "left", "right", "top", and "bottom" by assuming that the direction u1 in the figure of the entire screen is horizontal.

In the region 201B, a monitor window 170 for checking a state of the measurement target person during measurement is displayed. By displaying a live video of the measurement target person during the measurement, it is possible to improve reliability of checking and determination of a signal waveform as will be described later. In FIG. 4, a display mode in which the entire measurement recording screen 201 is displayed in a display screen of the single display device 28 (see FIG. 1) is illustrated, but it may be possible to separately display the region 201A and the region 201B by two or more display devices.

Meanwhile, the hardware configuration of the information processing apparatus 50 illustrated in FIG. 3 is one example, and it may be possible to add another device. Further, it is assumed that the information processing apparatus 50 illustrated in FIG. 3 has the hardware configuration based on a personal computer (PC) for example, but embodiments are not limited to this example, and a mobile terminal, such as a tablet, may be adopted. In this case, it is sufficient to adopt a communication interface with a wireless communication function as the network I/F 105.

Functional Block Configuration of Information Processing Apparatus

Figure 5:
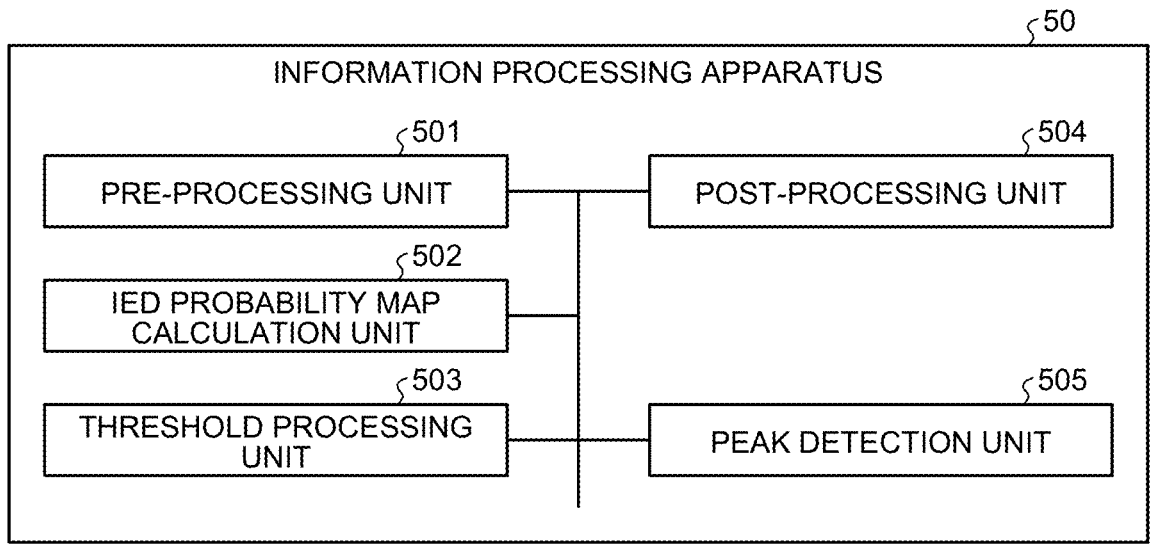
FIG. 5 is a diagram illustrating an example of a functional block configuration of the information processing apparatus.

FIG. 5 is a diagram illustrating an example of a functional block configuration of the information processing apparatus 50. The functional block configuration of the information processing apparatus 50 will be described below with reference to FIG. 5.

As illustrated in FIG. 5, the information processing apparatus 50 includes a pre-processing unit 501, an IED probability map calculation unit 502, a threshold processing unit 503, a post-processing unit 504, and a peak detection unit 505.

The pre-processing unit 501 performs pre-processing, such as downsampling, application of a frequency filter, extraction of a time window, or standardization of magnetic field data.

The downsampling is applied for adjustment to a sampling frequency that is used at the time of learning. Similarly, the same frequency filter as used in filtering that is adopted at the time of learning is applied. As the filter, a low-pass filter of 35 Hz, a bandpass filter of 3 Hz to 35 Hz, or the like is frequently used.

As a method of extracting the time window, a method of shifting the time window by a length of the time window without overlap, a method of overlapping a half of the length of the time window, a method of overlapping one-fourth of the length of the time window, or the like may be adopted. When the time windows are overlapped, averaging is performed for an overlapping portion at the time of calculation of an IED probability map to be described later.

As for the standardization of the magnetic field data, standardization is applied such that an average is zero and a distribution is 1 in the extracted time window. In addition to the standardization, it may be possible to use a normalization method such that a pre-set range of a magnetic field is −1 to 1.

The IED probability map calculation unit 502 calculates a probability map of a characteristic waveform (Interictal Epileptiform Discharge (IED)).

The IED indicates a certain waveform, such as spike wave, spike and wave, poly spike, poly spike and wave, or sharp wave, which is characteristic for an epilepsy lesion.

A normal nerve cell transmits, by synaptic transmission, a signal to a next nerve cell that constitutes a network. An ion charge flow (electric current) is a phenomenon of firing. In an abnormal firing phenomenon of epilepsy, innumerable nerve cells are triggered and fire approximately simultaneously to generate a large electric current. A waveform that is generated by the large electric current is the IED. The large electric current is called a dipole, and it is identified that a nerve cell as a focus of epilepsy is present at a position at which the dipole is generated (portion in which the electric current flows).

The threshold processing unit 503 narrows down, with use of a threshold, a time and a sensor region at/for which an IED probability is high from the IED probability map that is obtained by the IED probability map calculation unit 502.

The post-processing unit 504 performs post-processing for extracting a sampling time point and a sensor from the IED probability map that is subjected to the threshold processing by the threshold processing unit 503. Further, if a plurality of peaks are present (if two or more lesion parts are present) in the peak detection method or the map, the post-processing unit 504 performs post-processing for separating the map.

The peak detection unit 505 functions as an extraction means for extracting, by predetermined pattern matching, candidate peaks in a certain arbitrary period of time from at least one piece of waveform data, and a determination means for determining a single peak from among the candidate peaks of the waveform on the basis of a score related to the pattern matching. The peak detection unit 505 detects a peak of a spike by using the sensor and the sampling time point that are obtained before the peak detection unit 505.

The flow until a peak detection process will be described below.

Figure 6:
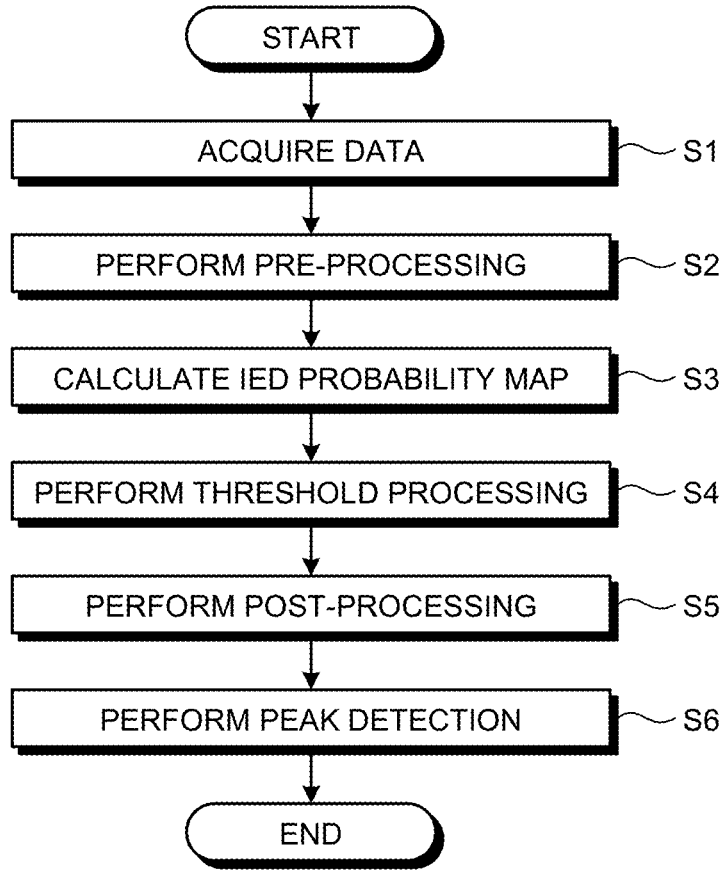
FIG. 6 is a flowchart illustrating the flow until a peak detection process.

FIG. 6 is a flowchart illustrating the flow until the peak detection process. Before the process, the measurement apparatus 3 performs measurement by the magnetoencephalogram, and outputs each piece of waveform data measured by the plurality of magnetic sensors of the dewar 31 to the server 40. The server 40 stores, in the data storage unit 42, each piece of waveform data measured by the plurality of magnetic sensors of the dewar 31 of the measurement apparatus 3.

Then, as illustrated in FIG. 6, the pre-processing unit 501 first acquires each piece of waveform data measured by the plurality of magnetic sensors of the dewar 31 of the measurement apparatus 3 from the data storage unit 42 of the server 40 (Step S1).

Subsequently, the pre-processing unit 501 performs pre-processing, such as downsampling, application of a frequency filter, extraction of a time window, or standardization of magnetic field data, on the pieces of acquired data (Step S2).

Then, the IED probability map calculation unit 502 calculates a characteristic waveform (IED) probability map (Step S3).

As for the calculation of the IED probability map, it may be possible to adopt a method of applying a model that is calculated by using machine learning, or it may be possible to adopt a conventional algorithm for detecting a spike position. If the machine learning is used, learning is performed by using a start part of dipole estimation as a correct answer; therefore, as compared to a conventional method of detecting a spike position, it is possible to obtain a result that is more similar to a start part of an IED that is manually selected by a doctor and a sensor that is manually narrowed down by the doctor.

Subsequently, the threshold processing unit 503 performs the threshold processing on the IED probability map that is obtained by the IED probability map calculation unit 502 (Step S4). Specifically, the threshold processing unit 503 narrows down, by using a threshold, a time at which the IED probability is high and a sensor region from the IED probability map that is obtained by the IED probability map calculation unit 502.

Then, the post-processing unit 504 performs post-processing for extracting a sampling time point and a sensor, which are used for dipole estimation, from the IED probability map that is subjected to the threshold processing by the threshold processing unit 503 (Step S5).

Further, if a plurality of peaks are present (if two or more lesion parts are present) in the peak detection method or the map, the post-processing unit 504 performs the post-processing unit 504 performs post-processing for separating the map.

Finally, the peak detection unit 505 performs peak detection by using the sampling time point that is obtained before the peak detection unit 505 (Step S6). For example, the peak detection unit 505 has a function to detect candidate peaks by pattern matching using machine learning or the like with respect to waveforms that have specific patterns and that are buried in noise, and has a function to determine, at this time, a peak by using a score that is quantified by predetermined procedures and conditions. In the present invention, the "score" that quantifies a certain concept, such as strength of pattern matching or a match rate between two waveforms, is used.

Here, one example of the peak detection process performed by the peak detection unit will be described in detail below.

The peak detection unit 505 sets time windows of certain arbitrary intervals prior to and posterior to the sampling time point. Then, the peak detection unit 505 searches for time points as candidate peaks with respect to data in the set time windows, and thereafter determines a peak point from the candidate peak points.

As a method of searching for the candidate peak points, it may be possible to adopt a method of searching for extreme values of a waveform in each of the sensors and determining times at which local maximum values and local minimum values appear as candidate peak points, a method of adopting, as the candidate peak points, times corresponding to tops of waveforms that exceed a predetermined upper limit and times corresponding to bottoms of the waveforms that exceed a predetermined lower limit, or the like.

As a method of determining the peak point, it may be possible to adopt a method of determining, as the peak point, a time at which the sensors with the candidate peak points are maximum, a method of determining, as the peak point, a time that is closest to the sampling time point that is obtained before the peak detection unit 505, or the like.

A method of displaying the peak point will be described below. The peak detection unit 505 functions as a display control unit that outputs display information for displaying a position of the peak.

Figure 7:
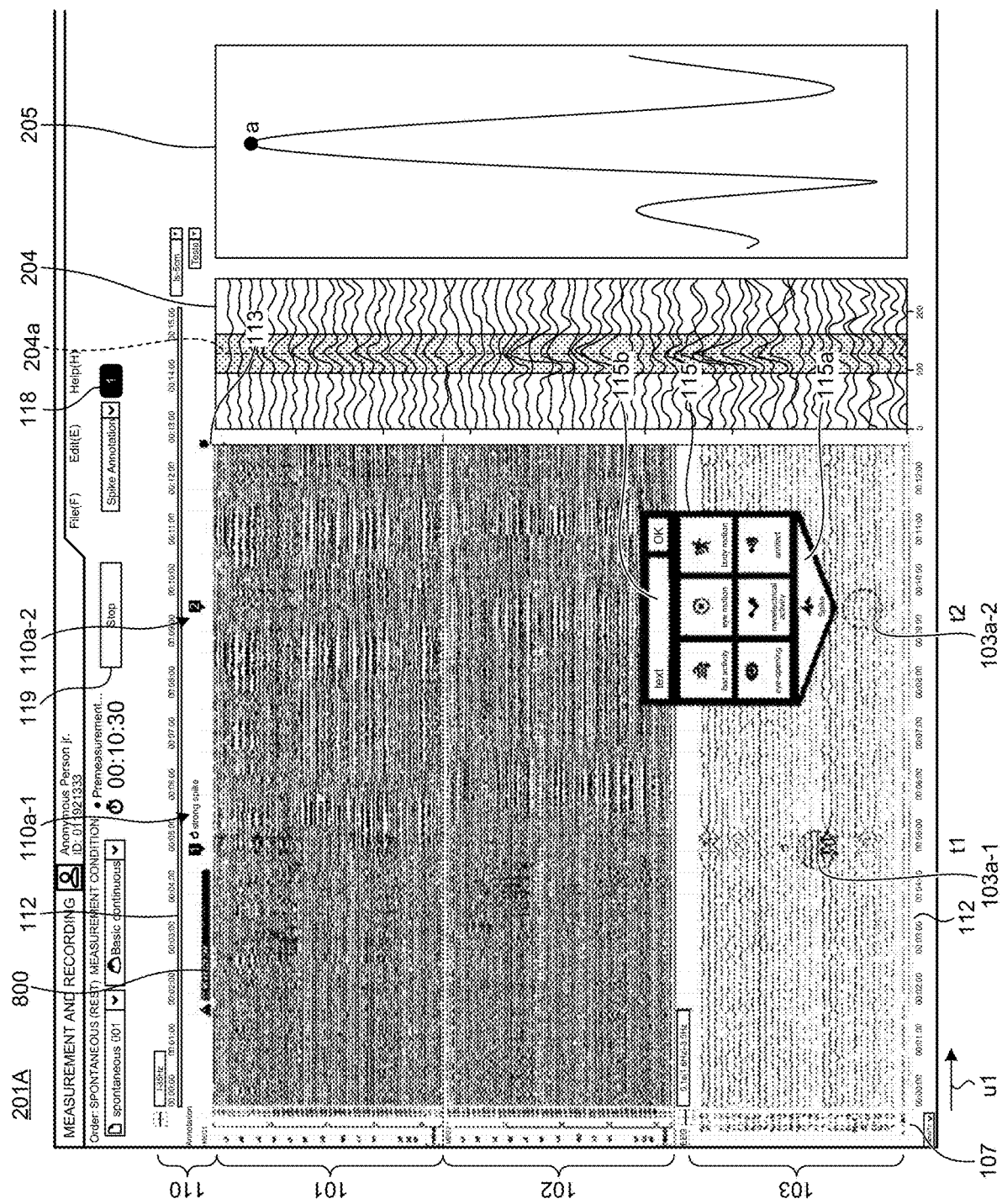
FIG. 7 is an enlarged view of a region 201A illustrated in FIG. 4.

FIG. 7 is an enlarged view of the region 201A illustrated in FIG. 4. The region 201A includes a display region 110 for displaying time information on signal detection, display regions 101 to 103 for displaying, in a parallel manner, a plurality of signal waveforms based on the signal detection, a display region 204 for displaying, in a parallel manner, a plurality of signal waveforms around the sampling time point that is used as a reference, and a display region 205 for displaying the peak point.

The time information displayed in the display region 110 is, in the example illustrated in FIG. 7, a time line including time display in which times (numerals) are assigned along a time axis 112, but it may be possible to display only a band-shaped axis without displaying times (numerals), or display only times (numerals) without an axis. Furthermore, as illustrated in FIG. 7, it may be possible to display the same time axis 112 below the display region 103, in addition to the time axis 112 in the display region 110.

A plurality of signal waveforms are displayed in a horizontal and parallel manner in the display regions 101 to 103.

As each of the signal waveforms, it may be possible to display only signal waveforms from the sensors in the same group, or may display signal waveforms from the sensors in different groups. Further, it may be possible to display signal waveforms from an electrode group individually or together with a different signal waveform. One or more kinds of signal waveforms among the above-described waveforms are displayed. Here, the same sensor group may be classified by, for example, a measurement site. In this example, waveforms are classified into waveforms of magnetoencephalography signals that are obtained from a group of magnetic sensors on a right side of a head portion of a measurement target person, waveforms of magnetoencephalography signals that are obtained from a group of magnetic sensors on a left side of the head portion of the measurement target person, and waveforms of electroencephalography signals that are obtained from electroencephalography electrodes on the measurement target person. Meanwhile, a combination of "the plurality of signal waveforms" is not limited to the above-described example. For example, it may be possible to arbitrarily select certain parts, such as a parietal region, a frontal lobe, and a temporal lobe, and selectively display signal waveforms that are obtained from sensors in each of the parts. A method of selecting the signal waveforms will be described in detail later.

In FIG. 7, waveforms of a plurality of magnetoencephalography signals that are obtained from the right side of the head portion of the measurement target person are displayed in the display region 101, waveforms of a plurality of magnetoencephalography signals that are obtained from the left side of the head portion of the measurement target person are displayed in the display region 102, and waveforms of a plurality of electroencephalography signals are displayed in the display region 103, where all of the waveforms are displayed in a horizontal and parallel manner. All of the signal waveforms are displayed on the same time axis in a synchronized manner. Each of the signal waveforms is displayed in association with a channel number 107 at which the corresponding signal is acquired, in particular, identification information on the electrode (for example, identification information on a reference electrode and a search electrode) or identification information on the sensor. In the present embodiment, it is assumed that the identification information on the electrode and the channel number have one-to-one correspondence, and the identification information on the sensor and the channel number have one-to-one correspondence, and, the identification information on the electrode, the identification information on the sensor, and the channel number are appropriately used in the description below. Meanwhile, embodiments are not limited to this example, and it may be possible to collectively associate a plurality of electrodes or a plurality of sensors with a channel number.

If measurement is started, measurement information is collected from each of the sensors and each of the electrodes, and signal waveforms are displayed horizontally in order of measurement time in a rightward direction (the direction u1) from the left edge in each of the display regions 101 to 103. A line 113 indicates a current time at which measurement is being performed, and moves rightward from the left edge of the region 201A. When the signal waveforms being displayed reach a right edge of the region 201A (a right edge of the time axis 112), the signal waveforms are gradually deleted from the left edge of the region 201A in the rightward direction, and new signal waveforms are sequentially displayed rightward from the left edge at deleted positions and the line 113 also moves rightward from the left edge. Accordingly, the time display on the time axis 112 is also updated in accordance with a range of an elapsed time of the new signal waveforms. Measurement and recording are continued until an "Exit Measurement" button 179 is pressed.

As a feature of the embodiment, when a measurer (recording person) recognizes waveform disturbance, amplitude singularity, or the like on the signal waveforms during data recording, it is possible to add a mark to the portion (portion of interest) on the signal waveforms. It is possible to designate a position and a range of the mark by pointer operation, click operation, or the like using a mouse. The portion of interest is displayed in an emphasized manner by displaying the mark on the signal waveforms in the display regions 101 to 103 and displaying a designation result at a position (corresponding time position) along the time axis 112 in the display region 110. Information on marking including the display along the time axis 112 is stored in a specific destination together with signal waveform data (biological data). Here, the "portion of interest" is used as a concept that includes not only a signal waveform at a certain point, but also a signal waveform in a certain range, and the same applies to below.

FIG. 7 illustrates a display mode in which, as one example, a range including waveforms (portions of interest) that are disturbed in one or more channels at a time t1 is designated in the display region 103. As illustrated in FIG. 7, the portion of interest is displayed by being emphasized by a mark 103a-1. Further, in the display region 110, an annotation 110a-1 indicating a designation result is displayed in an emphasized manner at a time position corresponding to the mark 103a-1. The emphasized display may be highlight display in the mark 103a-1, or may be display of an annotation in the vicinity of the mark 103a-1. Furthermore, in FIG. 7, waveforms are disturbed even at a time t2, and therefore, a mark 103a-2 and an annotation 110a-2 indicating a designation result are displayed with respect to this portion of interest.

While the mark 103a-1 and the mark 103a-2 having circular shapes are illustrated, but the marks 103a-1 and 103a-2 may have different shapes, such as rectangular shapes. For example, in the case of circular shapes, the mark 103a-1 is provided by designating a radius of the mark 103a-1 and designating a single point at which a center point of the mark 103a-1 is to be arranged. It may be possible to set a predetermined value in advance as the radius of the mark 103a-1, or it may be possible to allow the measurer to set an arbitrary value when designating the portion of interest. The same applies to the mark 103a-2.

Meanwhile, the annotation indicates that related information is added, as a note, to certain data. In the present embodiment, it is assumed that "annotation" without designation of any specific target represents a mark, an icon, or the like that is used to display the portion of interest in an emphasized manner. For example, in FIG. 7, the mark 103a-1, the mark 103a-2, the annotation 110a-1, and the annotation 110a-2 correspond to the "annotations". In the following, explanation will be given based on the assumption that any object that is used for emphasized display is included as one of the "annotations", without any explanation.

The annotation 110a-1 that is added at the time t1 in the display region 110 includes, as one example, an annotation identification number and information indicating an attribute of the waveform. In this example, an annotation number of "1", an icon representing the attribute of the waveform, and text information of "strong spike" are displayed.

If the measurer designates a different waveform portion or a neighboring region of the different waveform portion at the time t2, the designated portion is displayed in an emphasized manner by the mark 103a-2 in this example, and at the same time, an annotation number of "2" is displayed at the corresponding time position in the display region 110. Further, a pop-up window 115 for selecting the attribute is displayed at the position that is displayed in an emphasized manner. The pop-up window 115 includes selection buttons 115a for selecting various kinds of attributes, and an input box 115b for inputting a comment or additional information. In the selection buttons 115a, causes of waveform disturbance, such as "fast activity", "eye motion", "body motion", and "spike", are displayed as the attributes of the waveform. The measurer is able to check a state of the measurement target person by the monitor window 170 in the region 201B on the screen 201 (see FIG. 4), and therefore is able to appropriately select the attribute that indicates the cause of the waveform disturbance. For example, when a spike occurs in the waveform, it is possible to determine whether the spike indicates a symptom of epilepsy or whether the spike is caused by body motion (sneeze or the like) of the measurement target person.

Further, in addition to the checking method using the monitor window 170, it may be possible to arrange a sensor that detects motion of the measurement target person and may display a warning display 800 as illustrated in FIG. 7 in a detected period in the display region 110. For example, when the measurement target person moves his/her head, and if an amount of the movement exceeds an allowable amount, the warning display 800 is displayed. In the warning display 800, a sensor number for which data is not used as waveform data (biological data) is displayed. Therefore, the measurer is able to determine whether the spike indicates a symptom of epilepsy or the spike is caused by body motion (sneeze or the like) of the measurement target person. The warning display 800 may be displayed in a different color depending on a type of the "body motion" or depending on whether the motion is the "eye motion" or the "body motion".

Furthermore, in addition to display using the warning display 800, it may be possible to automatically input the attribute of the waveform provided in the pop-up window 115, on the basis of an output or the like from a sensor that detects motion of the measurement target person.

The same operation is performed at the time t1, and, in FIG. 7, the selection button 115a of the "spike" is selected and "strong spike" is input in the input box 115b in the pop-up window 115, so that the annotation 110a-1 is displayed in the display region 110. In the display mode as described above, when a large number of signal waveforms are displayed in a synchronized manner, it is possible to visually and easily identify portions of interest in the signal waveforms on the same time axis 112, and it is possible to easily recognize basic information on the portions of interest.

A part or all of the annotation 110a-1, for example, at least one of the attribute icon and the text annotation, may be displayed in the vicinity of the mark 103a-1 on the signal waveforms in the display region 103. Addition of the annotation on the signal waveforms may disturb checking of waveform shapes; therefore, when the annotation is to be displayed on the signal waveforms in the display regions 101 to 103, it is preferable to allow selection of display and hide of the annotation.

A counter box 118 displays a cumulative number of spike annotations. Every time the "spike" is selected, a counter value of the counter box 118 is incremented, so that it is possible to recognize, at a glance, a total number of spikes from the start of recording to a current time (the line 113).

In the display region 204, a dotted line 204a indicates the sampling time point that is used as a reference. In the display region 204, signal waveforms that are obtained by a plurality of sensors and that have spikes around the sampling time point are displayed in a parallel and enlarged manner. With the enlarged display of the signal waveforms in the display region 204, an analyst is able to re-confirm validity of the portion that is marked at the time of recording, or check a waveform portion that has not been checked at the time of measurement and recording. For example, by dragging the dotted line 204a to the left or right, it is possible to identify a correct portion of waveform disturbance or singularity and correct the portion. Further, it is possible to designate a type of a signal waveform (electroencephalogram waveform, magnetoencephalogram waveform, or the like) or a channel range to be displayed in the display region 204.

A position of the dipole moves while a certain time, such as dozens of milliseconds (msec), passes. The reason for this is considered that nerve cells that generate an epileptic signal are, as a bundle, electrically connected to one another with certain directivity. Further, it is assumed that the signal waveform of each of the sensors is determined by two phenomena, such as a change in intensity of the electric current due to appearance and disappearance of the dipole and a change due to movement of the dipole.

As described above, the sensors of the measurement apparatus 3 are arranged so as to cover the head portion, and distances to the dipole are different among the sensors. At a position close to the dipole, intensity of a magnetic field signal is increased in accordance with the Biot-Savart law. If the distance to the dipole increases, intensity of the magnetic field signal decreases. Consequently, the waveform is deformed.

Figure 8:
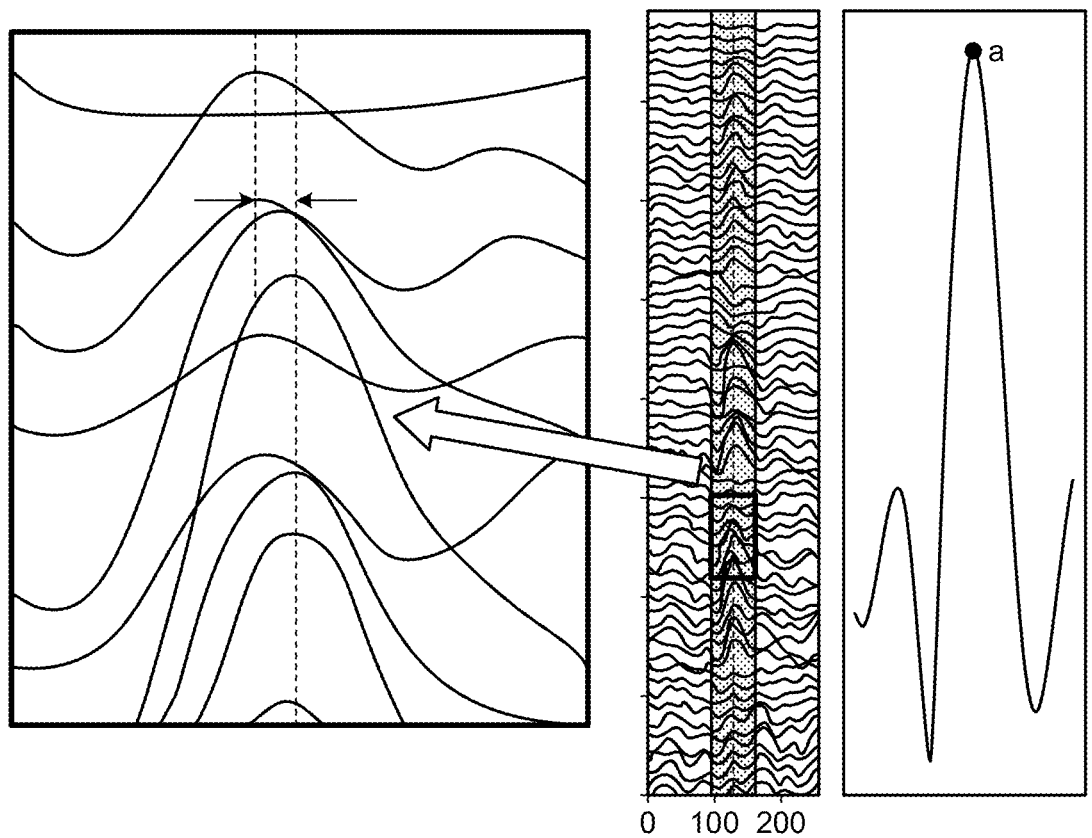
FIG. 8 is a diagram illustrating an example of peak shift due to movement of a dipole.

When the signal waveforms of the plurality of sensors of the measurement apparatus 3 are displayed in a parallel manner as illustrated in the display region 204, it is difficult to visually determine a reference point due to deviation among peaks caused by movement of the dipole as illustrated in FIG. 8.

To cope with this, in the present embodiment, as illustrated in the display region 205, a peak point of a waveform in a time interval that is colored in the display region 204 is displayed. As illustrated in the display region 205, for example, extreme values of the waveform of each of the sensors are searched for, times at which local maximum values and local minimum values appear are adopted as candidate peak points, and a time at which the sensors with the candidate peak points are maximum is displayed as the peak point. If a point at which the value of a waveform is maximum among the local maximum values is adopted as a peak, a point of a local maximum value a (a point) is adopted as the peak. In the spike waveforms of the plurality of sensors in the display region 204, a time corresponding to the a point is indicated by a dotted line.

In this manner, according to the present embodiment, by detecting a peak portion of a spike time that is determined from the time series of the plurality of sensors, it is possible to determine a reference point that is used when analyzing a dipole.

The present invention has a function to detect candidate peaks by pattern matching using machine learning or the like with respect to waveforms that have specific patterns and that are buried in noise, and has a function to determine, at this time, a peak by using a score that is quantified by predetermined procedures and conditions. In the present invention, the "score" that quantifies a certain concept, such as strength of pattern matching or a match rate between two waveforms, is used.

Conventionally, when determination is performed visually and manually, the determination is performed in an analog manner and may be inconsistent. In contrast, by quantification under an objective and predetermined rule, objectivity and reproducibility are improved as compared to determination made by a person. Specifically, as a method of extracting candidates, a calculation method using a correlation coefficient between a teacher waveform and a candidate waveform may be used. It is possible to adopt a method using a Pearson correlation coefficient (r) of data rows of the teacher data waveform and the candidate waveform in the same interval. It is possible to use a value of r as the score. However, in this case, as a method of removing noise of the waveforms, it is required to ensure that waveforms around the peak are not disturbed, by drawing a base line for each certain interval, for example. If noise removal using the base line is not successfully performed, in particular, if myoelectric artifact of the head portion, such as a temple, is not removable, it may be possible to use a Spearmans's rank correlation coefficient (rs) or the like as the score. Further, the method of qualifying the matching is not limited to the above-described example, and it may be possible to use a method of quantifying a correlation based on a certain formula.

The same score is always calculated with good reproducibility for the same waveform. By appropriately setting a score value that is used as a threshold for extraction, an extracted waveform that is similar to the teacher waveform data has always the same waveform and in the same interval as the teacher waveform data, and reproducibility is more improved than visual and manual extraction. However, if innumerable and various pieces of teacher data are prepared, a correct answer rate is reduced; therefore, it is important to prepare the teacher data by an appropriate method based on determination made by a doctor. If a large number of pieces of teacher data are used, a large number of correlation coefficients (r) are present. In this case, it is possible to obtain a result with good reproducibility by mechanically representing an alternative score by using an average value of the plurality of correlation coefficients (r) and performing comparison.

A position of the peak is determined in the peak waveform that has a certain score and that is similar to the teacher data. To determine the peak, in addition to a simple method of determining a maximum value and a minimum value in a certain time interval, it may be possible to adopt a method of performing leveling in the certain interval and thereafter determining a maximum value and a minimum value. In this example, patterns that are extracted by using a specific pattern are adopted as candidates, and therefore, selection is performed from among approximately similar waveforms. Spikes of epileptic abnormal wave described in the present embodiment often arise as a waveform with three extrema, and it is likely that a second inflection point is maximum or minimum among three inflection points (a local maximum value and a local minimum value value).

It is necessary to give a notice of the peak position that is determined as described above to a user, such as a doctor. To give the notice, as illustrated in FIG. 7, a user interface that clearly indicates the peak position is used. As a method of clarification, by investigating a situation in which a doctor or a care-giver as the user views the screen and optimizing the method in accordance with the situation, a method that allows the user to recognize the peak position without an error is adopted. Further, it may be possible to provide a function to attract attention by buzzer sound or voice to allow the user to recognize a notice even when the user is not viewing the screen. By allowing automatic detection of the peak position, even if a care-giver or a doctor is concentrated and does not pay attention to the peak position, it is possible to accurately detect the peak position and give a notice of an accompanying event (epilepsy or getting out of bed).

Meanwhile, the peak detection unit 505 is able to enhance a search area when searching for extreme values. In some cases, it may be possible that a spike waveform does not appear in a time window that is determined in advance. Considering the situation as described above, if the peak is not detected, it is effective to enhance the search area for searching for extreme values.

Second Embodiment

A second embodiment will be described below.

The second embodiment is different from the first embodiment in that a waveform synthesis process is added. In the following description of the second embodiment, explanation of the same components as those of the first embodiment will be omitted, and differences from the first embodiment will be described.

Figure 9:
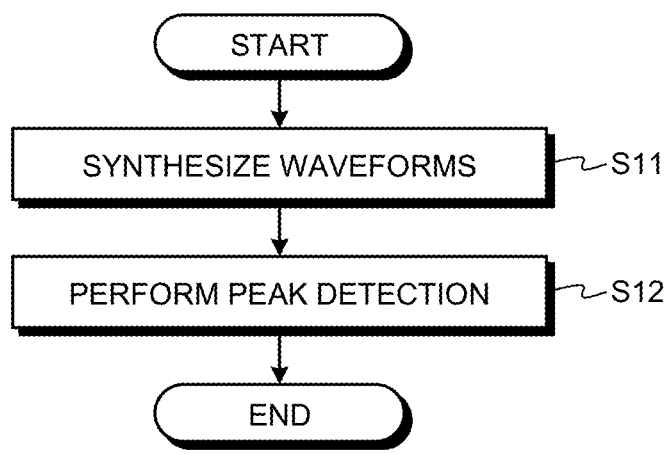
FIG. 9 is a flowchart illustrating the flow of a peak detection process performed by a peak detection unit according to a second embodiment.

FIG. 9 is a flowchart illustrating the flow of a peak detection process performed by the peak detection unit 505 according to the second embodiment.

After the sampling time point is detected similarly to the first embodiment, as illustrated in FIG. 9, the peak detection unit 505 sets time windows of certain arbitrary intervals prior to and posterior to the sampling time point, and performs a waveform synthesis process of forming a single synthesized waveform using all pieces of acquired sensor information (Step S11). In other words, the peak detection unit 505 functions as a waveform adding means of generating synthesized wave data by synthesizing pieces of waveform data in the same time interval in the extracted waveform data.

As a method of synthesizing waveforms, a method of defining a base line for the waveforms in the set time windows and calculating difference values with respect to the base line is effective.

First, the peak detection unit 505 defines a base line of the waveforms. As a method of calculating the base line, it is possible to adopt a method of calculating an average in each time direction or a method of calculating an average in each of sensor directions. As a method of calculating the difference values, it is possible to calculate a synthesized waveform by a method of averaging or adding up absolute difference values of the respective sensor values with respect to the base line at each time, or a method of averaging or adding up difference values of the respective sensors with respect to the base line.

By synthesizing the waveforms as described above, it is possible to generate a waveform in which information on the plurality of sensors is taken into account.

Meanwhile, in the waveform synthesis process at Step S11, it may be possible to synthesize the waveforms in a time range with a high IED probability on the basis of the probability map that is obtained by the IED probability map calculation unit 502.

Subsequently, the peak detection unit 505 searches for a time of a peak of the spike waveform by using the synthesized waveform that is obtained through the waveform synthesis process. The peak detection unit 505 searches for points of extreme values with respect to the synthesized waveform, and determines an extreme value that meets a certain condition as the peak (Step S12). At this time, the following conditions may be used as the condition, for example.

(1) a point at which a value of the synthesized waveform is maximum or minimum among points of local maximum values or local minimum values
(2) a point at which a value of the synthesized waveform is maximum among local maximum points for which immediately prior and immediately posterior extreme points are local minimum points
(3) a point at which the synthesized waveform is maximum among local maximum points for which immediately prior extreme points have local minimum values Due to the characteristics of the spike waveform, both of a positive peak and a negative peak may be present. In the method of adding up or averaging the absolute difference values with respect to the base line at the time of calculating the synthesized waveform, the synthesized waveform has a large value in the vicinity of the peak independent of the polarities, and therefore, it is possible to determine the peak from among the local maximum values among the retrieved extreme values.

Figure 10:
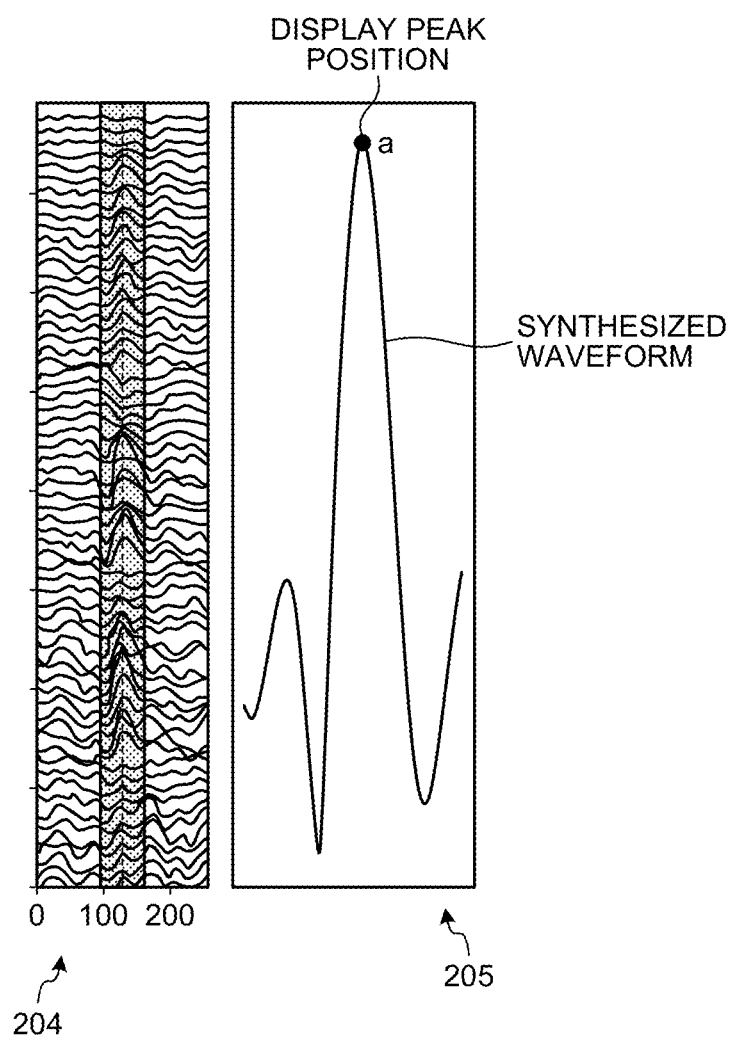
FIG. 10 is a diagram illustrating a display region for displaying a peak point.

FIG. 10 is a diagram illustrating the display region 205 for displaying a peak point. In the display region 205 illustrated in FIG. 10, the peak point in a result that is obtained by performing waveform synthesis of waveforms in the time interval colored in the display region 204. In the synthesized waveform illustrated in the display region 205, if a point at which a value of the synthesized waveform is maximum among local maximum values is adopted as the peak, the point of the local maximum value a is adopted as the peak. In the spike waveforms of the plurality of sensors in the display region 204, the time corresponding to the a point is indicated by the dotted line.

Figure 11:
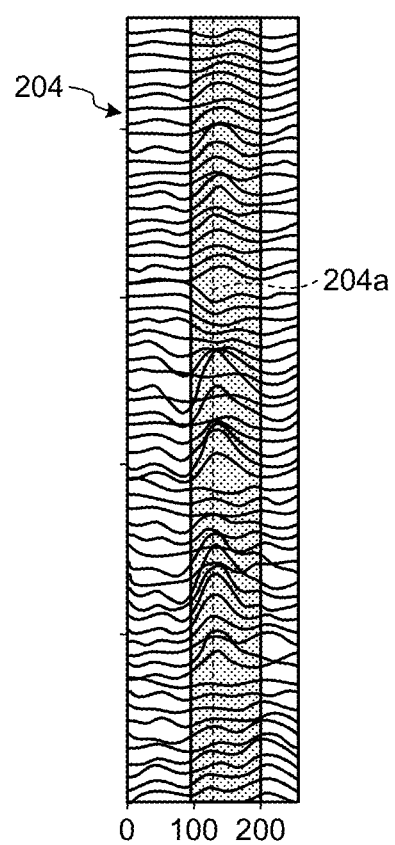
FIG. 11 is a diagram illustrating an example of a time window selection range for waveform synthesis.

FIG. 11 is a diagram illustrating an example of a time window selection range for waveform synthesis. As illustrated in FIG. 11, the peak detection unit 505 is able to perform waveform synthesis by acquiring sensor information in different time widths prior to and posterior to the sampling time point. In FIG. 11, a dotted line indicates the sampling time point and a colored time interval indicates a width of the time window in which the waveform synthesis is performed. Due to the characteristics of the spike waveform, a time from the peak to an end part is longer than a time from the start part to the peak. Therefore, with use of this method, the probability that the spike waveform is included in the time window is further improved.

In this manner, according to the present embodiment, by generating synthesized data in which pieces of waveform data in the same time interval are synthesized, it is possible to represent peaks that are generated at different times in the plurality of sensors by a single waveform.

In the first embodiment as described above, the example has been described in which the match rate between waveforms that are generated at the time of an event is calculated as the score by waveform matching using machine learning or the like. The match rate is quantified as the "score" with good reproducibility.

The "score" as the match rate can be calculated for a large number of time intervals with respect to a waveform that is output by a single sensor. For example, if waveform data in a time interval of 1000 msec is present, it is possible to generate 900 pieces of waveform data by shifting a time interval of 100 msec at a pitch of 1 msec. 900 Pearson correlation coefficients r are present as scores indicating whether the 900 pieces of waveform data match the teacher data. For example, if an epileptic abnormal wave is generated only once during the period of 1000 msec, only one of the 900 Pearson correlation coefficients r has a high value. It is important to set an appropriate threshold such that the single coefficient can be determined. However, if the pitch of 1 msec is changed to, for example, a pitch of 0.1 msec, a pitch of 0.01 msec, or the like, the number of correlation coefficients is increased in a range of about 0.5 msec prior to and posterior to around the time at which the epileptic abnormal waveform is generated. In this case, it may be possible to set the threshold such that the threshold is exceeded a plurality of number of times around the time at which epilepsy occurs, instead of assuming that the threshold is exceeded only once.

In contrast, the synthesized wave data of the present embodiment is based on the assumption that the pieces of waveform data of the plurality of sensors are synthesized. For example, in a case of a magnetoencephalogram with 100 channels, 100 waveforms are present. Similarly to the description as described above, it is assumed that a time interval of 100 msec is shifted at a pitch of 1 msec with respect to a waveform in 1000 msec. Similarly to the description as described above, if it is assumed that 900 Pearson correlation coefficients r are present for 1 channel and if 100 channels are provided, 90000 correlation coefficients are present. If an epileptic abnormal wave is generated, in the time interval, the Pearson correlation coefficients in some of the channels exceed the threshold. Pieces of waveform data in some channels in each of which the threshold is exceeded are extracted. Only the pieces of waveform data in the channels in each of which the threshold is exceeded in the same time interval are synthesized. In other words, the time interval in which the threshold is exceeded is selected, and the sensors that exceed the threshold are selected in the same time interval.

The synthesized waveform that is obtained as described above is displayed on the screen of the interface as illustrated in FIG. 10. The synthesized waveform illustrated in the screen makes it possible to easily perform determination as compared to determination by a glance of a plurality of waveforms. This is because the user pays attention to only the single synthesized waveform in a concentrated manner. By selecting appropriate sensors and synthesizing the waveforms, event waveforms due to epilepsy or going out of bed are represented by a single waveform. As compared to a case in which the plurality of waveforms are viewed in a listed manner, the synthesized wave of the selected waveforms for which noise is reduced is used as information with improved visibility. Therefore, a doctor or a care-giver is able to determine an event only by taking a brief look at the synthesized waveform.

In the present embodiment, the sensors are selected by the waveform data. This means that sensors located away from a focus of the epilepsy are eliminated. In other words, it is possible to eliminate a sensor with large noise and a sensor in which a signal does not appear. As for the synthesized waveform of the sensors that are selected as described above, noise is reduced and automatic detection accuracy is improved. By performing automatic detection with high accuracy, it is possible to provide a result by, as in the interface illustrated in FIG. 10, outputting buzzer sound or providing a display marker with good visibility. This not only simply improves the visibility of the waveform, but also improves accuracy and ease of determination by attracting attention of a user.

Meanwhile, in the first embodiment and the second embodiment, a time window of a certain period of time is set with reference to the sampling time point, and peak detection is performed by using all pieces of sensor information. At this time, the peak detection unit 505 may calculate a sensor value by adding a weight to a sensor with a characteristic waveform in accordance with the probability that is obtained by the IED probability map calculation unit 502, and may perform peak detection as described in the first embodiment or waveform synthesis as described in the second embodiment by using the calculated value. Assuming that the probability obtained by the IED probability map calculation unit 502 at a certain time is represented by p, and a value of a certain sensor is represented by x, a weighted sensor value $x_{weight}$ is represented by Expression (1) below. Further, the probability p may be normalized.

$$x_{weight} = px \quad (1)$$

In this manner, with use of the weighted value of the waveform information on the sensor having the characteristic waveform at a certain time, it is possible to improve peak detection accuracy as compared to simple calculation of an average or a total sum of all of sensors at all of times.

Furthermore, the peak detection unit 505 may perform the peak detection as described in the first embodiment or the waveform synthesis and the peak detection as described in the second embodiment by using the information on the sensor and the sampling time point that are extracted by the post-processing unit 504.

With this configuration, in the process until the post-processing unit 504, the sensor with the high probability in the IED probability map is determined through the threshold processing, and therefore, as compared to a case in which a weight is added to the sensor with the characteristic waveform as described above, it is possible to perform analysis by using only the sensors with more characteristic waveforms.

Figure 12:
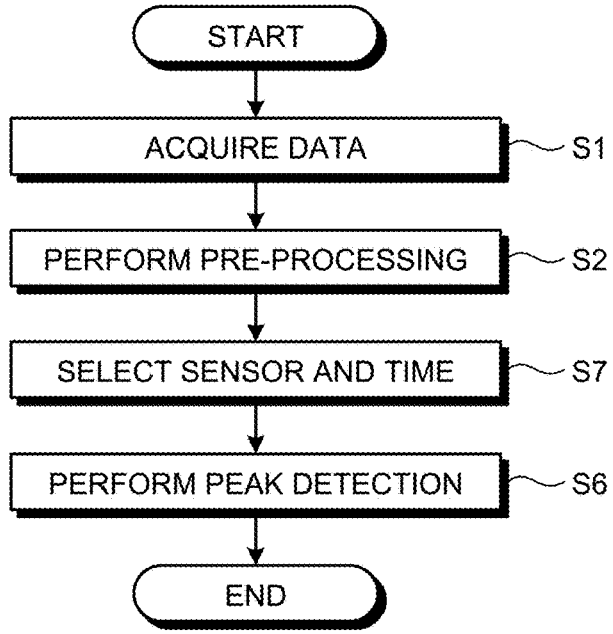
FIG. 12 is a flowchart illustrating the flow until a peak detection process according to a modification.

FIG. 12 is a flowchart illustrating the flow of a peak detection process according to a modification. As illustrated in FIG. 12, it may be possible to perform a sensor/time selection process (Step S7) instead of the IED probability map detection process (Step S3), the threshold processing (Step S4), and the post-processing (Step S5) as illustrated in FIG. 6. Specifically, the information processing apparatus 50 may allow manual selection of a sensor and a time in the region 201A illustrated in FIG. 7. The peak detection unit 505 extracts a sensor with a spike waveform and the sampling time point on the basis of visual determination that is performed by the doctor (Step S7), and performs peak detection by using an extraction result (Step S6).

If the sensor and the time are manually selected, by cooperation with a user interface (UI) with the screen as illustrated in FIG. 7, the doctor is able to check waveforms, select the sampling time point and sensors, and record the sampling time point and the sensors.

Figure 13:
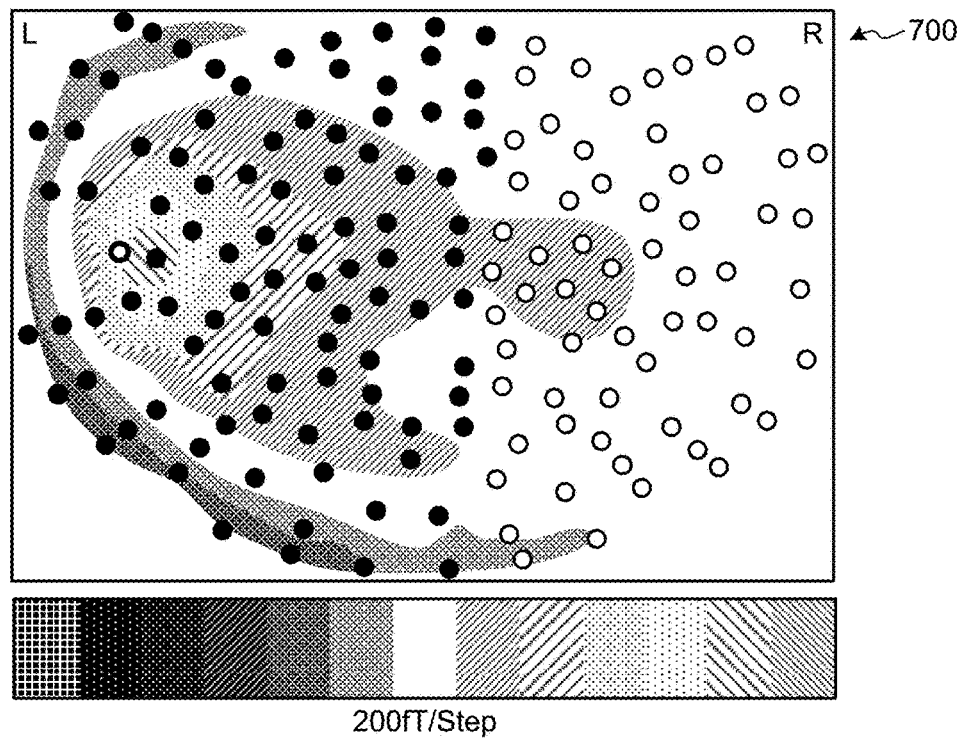
FIG. 13 is a diagram illustrating an example of a UI that represents magnetic fields on a scalp.

Meanwhile, as a method of visually extracting a sensor, it may be possible to perform determination from a magnetic field distribution on the actual scalp, instead of extraction from the waveform information as illustrated in the UI with the screen as illustrated in FIG. 7. FIG. 13 is a diagram illustrating an example of a UI that represents magnetic fields on a scalp. In a UI 700 illustrated in FIG. 13, a magnetic field value obtained by each of the sensors at a certain time is represented by a certain color to represent the magnetic fields on the scalp. By cooperating with the UI 700 that can record the selected sensor as illustrated in FIG. 13, the peak detection unit 505 is able to select a necessary sensor from a distribution map of the magnetic fields on the scalp.

Meanwhile, in each of the embodiments as described above, the example has been explained in which the magnetoencephalogram is used as the measurement apparatus 3, but embodiments are not limited to this example, and the present invention may be applied to an information processing apparatus, such as an electroencephalogram or an electrocardiogram, that processes signals measured by a plurality of sensors.

First Modification

A first modification in which a bed sensor is adopted as the measurement apparatus 3 will be described below.

Figure 14:
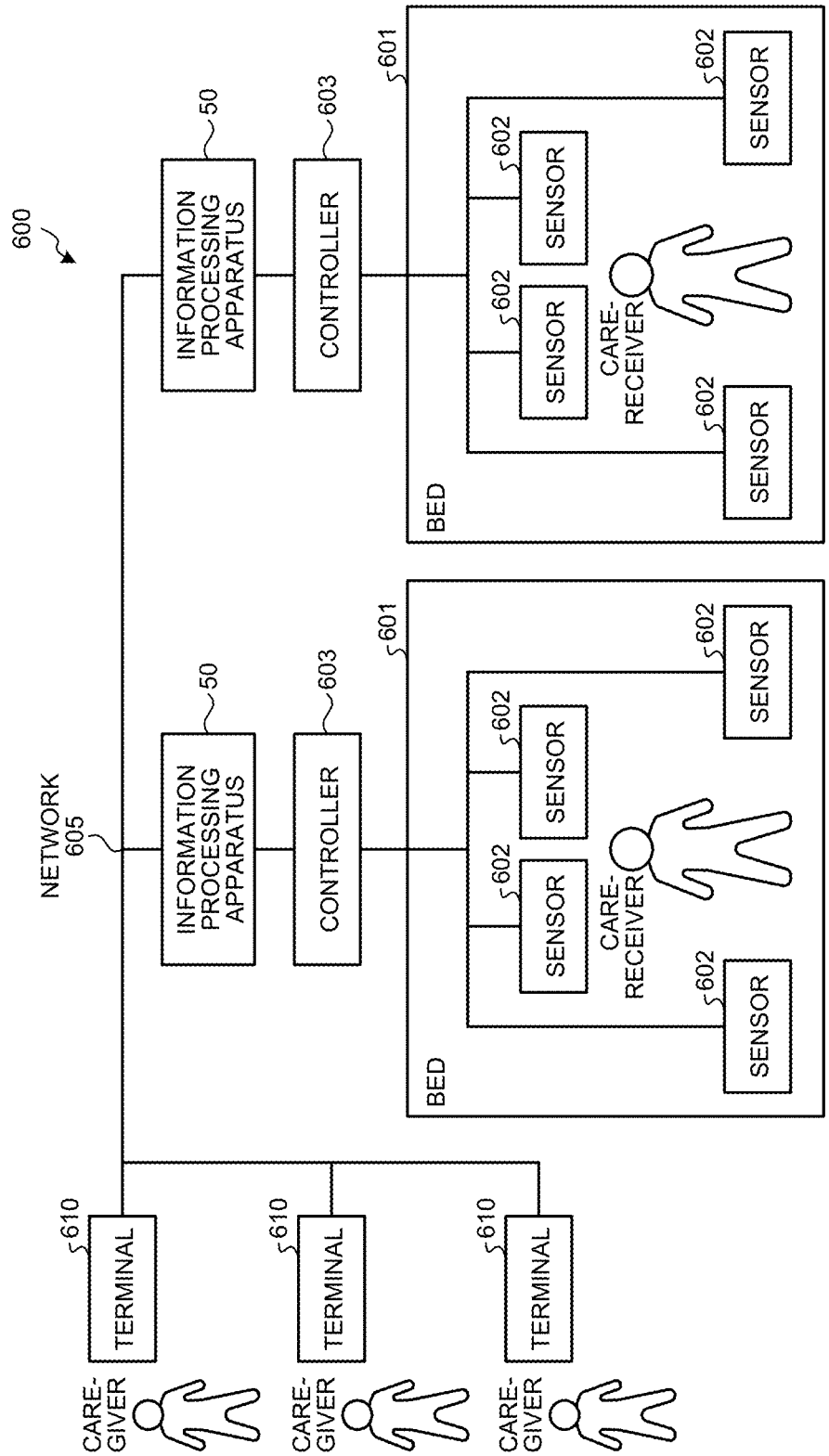
FIG. 14 is a system configuration diagram illustrating a configuration of a bed sensor system according to a first modification.

FIG. 14 is a system configuration diagram of a bed sensor system 600 according to the first modification. In the first modification illustrated in FIG. 14, the bed sensor system 600 for detecting going out of bed, which is used in a nursing facility, will be described. Similarly to each of the embodiments as described above, with use of the present invention, it is possible to automatically process and analyze data from complicated waveform data and convert a form of the data to a certain form, such as a waveform peak or an alarm, that can easily be recognized by a person (a doctor or a caregiver).

First, a nursing facility, to which the first modification is applied, and a background of the technology will be described. In the nursing facility, a care-receiver may stand up from a bed 601 and may fell and be insured while a care-giver is not paying attention to the care-receiver. It is often the case that, when the care-receiver stands up to go to the bathroom or the like, the care-receiver may fall by sliding his/her feet and fracture the lumbar spine, which leads to a serious injury for the care-receiver. The care-giver needs to pay attention to standing up from the bed 601 (going out of bed) of the care-receiver as much as possible. In particular, if the care-receiver has a leg problem, a waist problem, dementia, or the like, the care-receiver may always need assistance to get out of bed.

However, at midnight for example, it is in reality difficult for the care-giver to continuously watch over behaviors of a single care-receiver. Further, the nursing facility may have individual rooms, and it is in reality difficult to perform monitoring using cameras because of privacy reasons. Therefore, a system in which a sensor is installed in the bed 601 to monitor a timing at which the care-receiver gets out of bed is used. If it is possible to automatically and accurately detect a getting-out-of-bed timing, it is possible to issue an alarm at the detected timing to give a notice to the care-giver. With this system, it is possible for the care-giver to avoid spending a long time for watching over, and it is possible to assist getting out of bed or going to the bathroom at a good timing, so that it is possible to prevent a falling accident. Furthermore, by processing and recording waveforms continuously for 24 hours, rather than detecting getting out of bed in a timely manner, it is possible to recognize the frequency of "getting out of bed" in a day and times of the getting out of bed in the day. By statistically processing the course of events in 24 hours, it becomes possible to pay attention even to a physical condition, such as sleeping hours, of the care-receiver.

The bed sensor system 600 illustrated in FIG. 14 includes load sensors 602 on four legs of the bed 601. The information processing apparatus 50 detects a load state on the bed 601 by the load sensors 602, determines whether a care-receiver gets out of bed by reading a temporal change (waveform) of the load state, and detects an action of getting out of bed immediately before the action occurs.

The load sensors 602 are sensors that quantify an amount of load, and in general, a piezoelectric element, a strain gauge, or the like is used. In the first modification, a strain gauge is adopted as each of the load sensors 602. The strain gauge detects a shape change of a rigid body caused by a load as a change of a wiring distance of a fixed resistor wire and an accompanying change of electrical resistance. In the first modification, a bridge circuit is adopted because a change of the electrical resistance is minute. The bridge circuit is able to improve detection sensitivity for electrical resistance, and reduce a temperature change as much as possible. A change in the load is represented as a change in voltage applied to bridge resistance, and is converted to an appropriate voltage value by an amplifier.

As illustrated in FIG. 14, the four load sensors 602 are installed in the single bed 601, and a controller 603 once collects information, i.e., pieces of data of the load sensors 602. The controller 603 transmits the pieces of collected data to the information processing apparatus 50. The information processing apparatus 50 performs information processing to be described later, and sends, on an as-needed basis, an alarm indicating getting out of bed to a terminal 610 that is carried by the care-giver via a network line 605. As the network line 605, communication based on a general standard, such as Wi-Fi (registered trademark) or Bluetooth (registered trademark), may be used.

Figure 15:
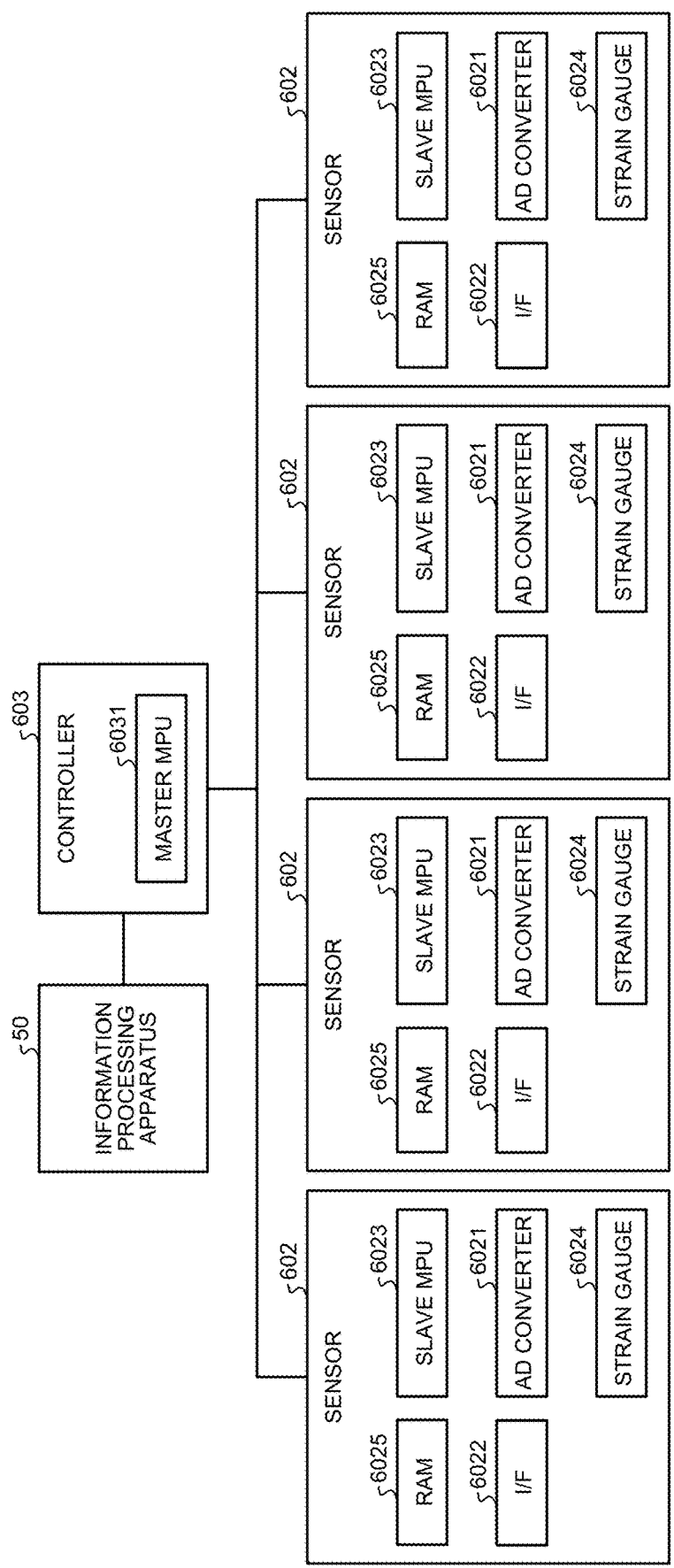
FIG. 15 is a block diagram illustrating configurations of load sensors.

FIG. 15 is a block diagram illustrating a configuration of the load sensors 602. As illustrated in FIG. 15, each of the load sensors 602 includes an analog-to-digital conversion element (AD converter) 6021, a transmission element (I/F) 6022, a crystal oscillator, a slave microprocessor (MPU) 6023, a RAM 6025, a clock receiving element, a strain gauge 6024, an amplifier, and the like. As the crystal oscillator of the load sensor 602, a crystal oscillator with accuracy of about 100 ppm is adopted. Therefore, it is possible to maintain clock accuracy of about 10 msec by receiving a signal from a master MPU 6031 of the controller 603 for calibration once every three minutes and correcting a timing, for example.

An output from the strain gauge 6024 is amplified up to hundreds mV level at maximum by a connected strain amplifier. The analog signal is converted to a digital signal by the AD conversion element. As the AD converter 6021, an element that outputs 12-bit detection value data at 10-Hz cycle is adopted. The detection value data is transmitted to the slave MPU 6023 by I2C communication.

The slave MPU 6023 temporarily simultaneously stores therein a received sensor detection value and a timestamp in a parallel manner in a storage unit in the slave MPU 6023. This will be referred to as a data set. The timestamp is synchronized with the master MPU 6031 of the controller 603 at the level of 10 msec by calibration as described above. The slave MPU 6023 transmits the stored data set, at an appropriate timing, to the master MPU 6031, together with a header signal including an identification number of the slave MPU 6023.

The master MPU 6031 sequentially receives signals from the four slave MPUs 6023. The master MPU 6031 assigns an identification number to each of the four slave MPUs 6023, and temporarily stores a data set of three rows, such as the identification number, the timestamp, and the detection value data, in a memory element. Timestamp values may vary among the stored four load sensors 602 at the millisecond level, and therefore, each piece of data is interpolated and converted to a data set of 100 msec. As for the interpolation of the detection value data, linear interpolation is performed on five pieces of prior and posterior detection value data to determine a value. Consequently, a data set of five rows, in which the pieces of detection value data of the four load sensors 602 are aligned by using the same timestamp is completed. The controller 603 transmits the data set to the information processing apparatus 50 and stores the data set in a storage unit in the information processing apparatus 50.

The information processing using the data set will be described below.

Figure 16:
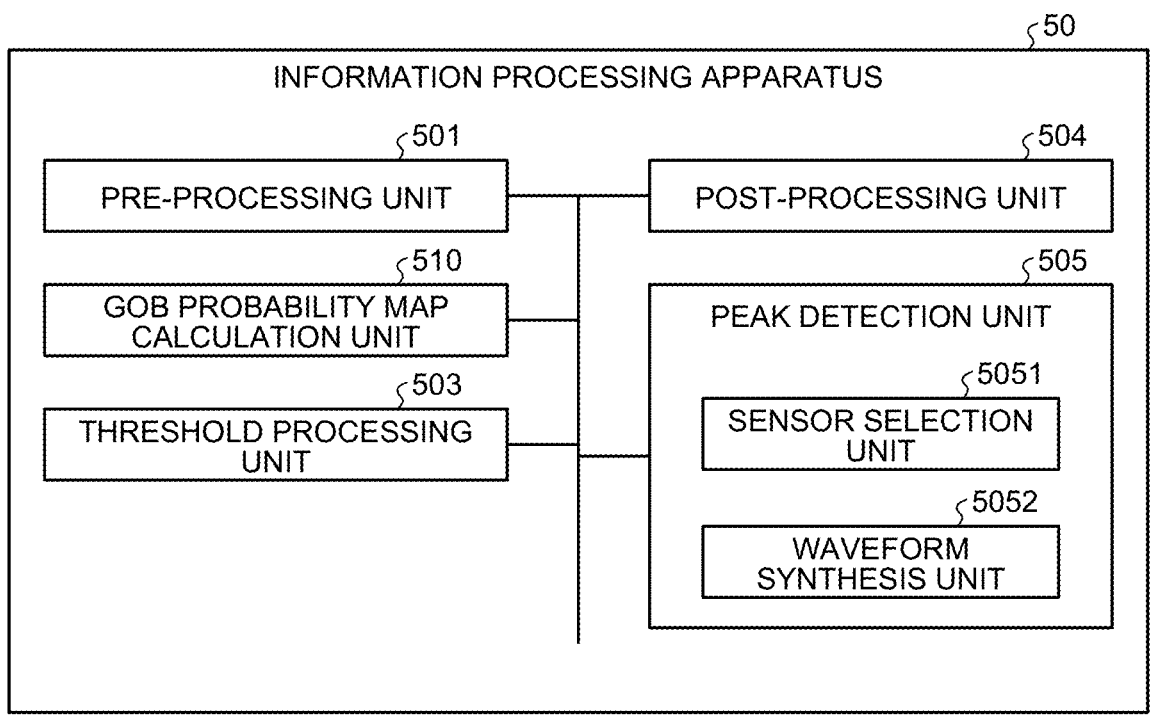
FIG. 16 is a diagram illustrating an example of a functional block configuration of an information processing apparatus.

FIG. 16 is a diagram illustrating an example of a functional block configuration of the information processing apparatus 50 according to the first modification. As illustrated in FIG. 16, the information processing apparatus 50 includes the pre-processing unit 501, the threshold processing unit 503, the post-processing unit 504, the peak detection unit 505, and a GOB probability map calculation unit 510 instead of the IED probability map calculation unit 502. Further, the peak detection unit 505 includes a sensor selection unit 5051 and a waveform synthesis unit 5052.

The pre-processing unit 501 performs pre-processing, such as downsampling, application of a frequency filter, extraction of a time window, or standardization of detection data.

The GOB probability map calculation unit 510 calculates a probability map for a characteristic waveform (getting out of bed (GOB)).

The threshold processing unit 503 detects, with use of a threshold, a time at which a GOB probability is high and the load sensor 602 for which the probability is high from the GOB probability map that is obtained by the GOB probability map calculation unit 510.

The sensor selection unit 5051 selects the appropriate load sensors 602 from among the four load sensors 602 on the basis of the probability that is quantified by the GOB probability map calculation unit 510. The sensor selection unit 5051 normally selects the three load sensors 602, but may select two or four sensors in accordance with a value. The waveform synthesis unit 5052 synthesizes the waveforms of the load sensors 602 that are selected at the selected time or in the selected period. Then, the peak detection unit 505 determines whether getting-out-of-bed occurs on the basis of the synthesized waveform.

The post-processing unit 504 issues an alarm for giving a notice to the care-giver, and provides information on a health condition in accordance with the frequency of getting out of bed.

Figure 17:
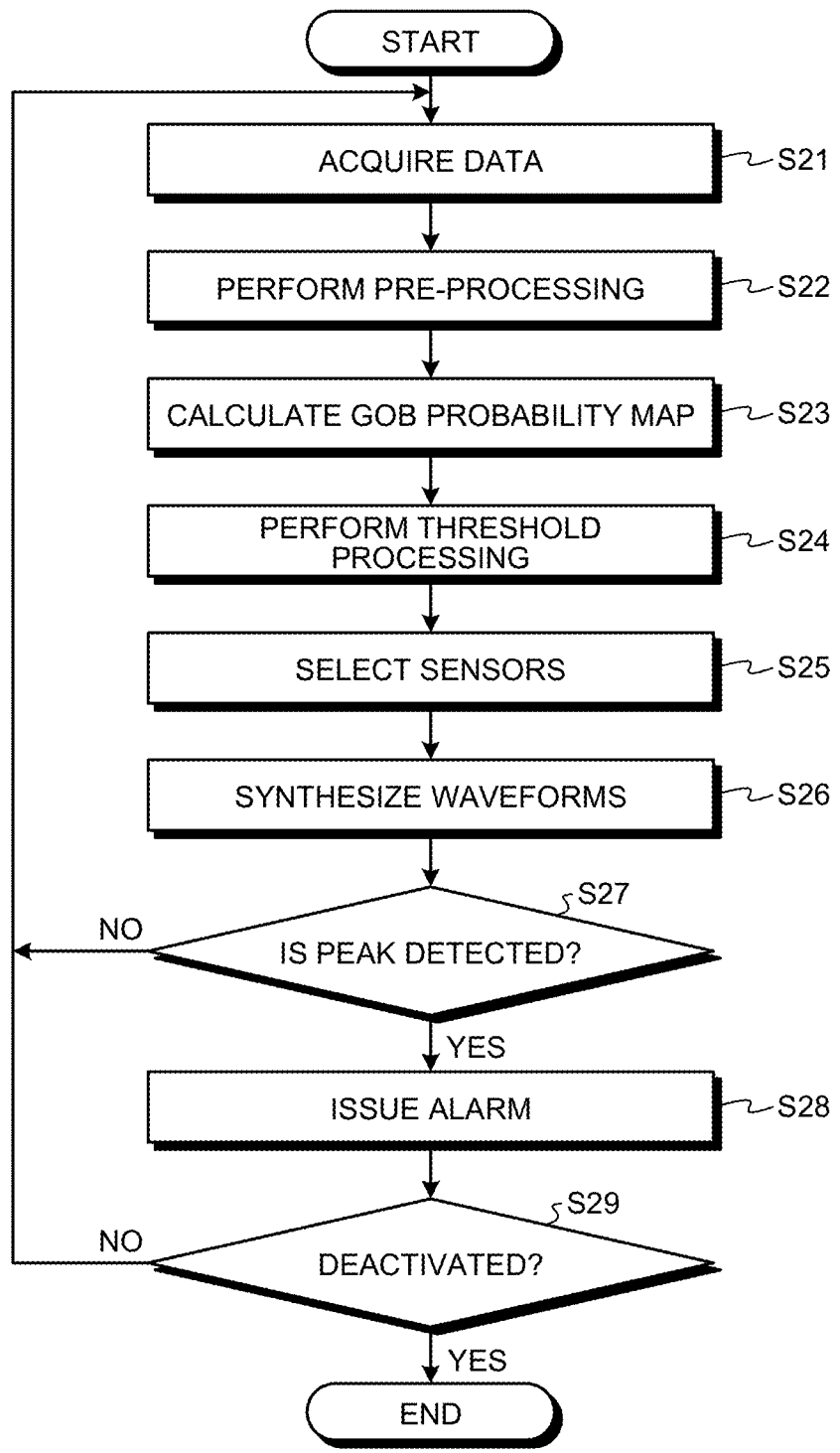
FIG. 17 is a flowchart illustrating the flow until a peak detection process.

FIG. 17 is a flowchart illustrating the flow until a peak detection process. As illustrated in FIG. 17, if the bed sensor system 600 starts operation, the controller 603 starts to acquire detection value data (Step S21). The controller 603 transmits each piece of waveform data measured by the load sensors 602 to the information processing apparatus 50 and stores each pieces of the waveform data in the storage unit.

Subsequently, the pre-processing unit 501 performs pre-processing, such as downsampling, application of a frequency filter, or extraction of a time window, on the acquired detection value data on the basis of the acquired waveform data (Step S22).

Then, the GOB probability map calculation unit 510 calculates a characteristic waveform (GOB) probability map (Step S23). As for the calculation of the GOB probability map, it may be possible to use a method of applying a model that is calculated by using machine learning. In the machine learning for GOB, getting-out-of-bed data on a subject in general activity conditions is learned. The getting-out-ofbed data is disclosed in, for example, Japanese Unexamined Patent Application Publication No. 2020-080121 or the like. The machine learning is disclosed in, for example, Japanese Unexamined Patent Application Publication No. 2021-069929 or the like. Meanwhile, there may be individual differences, such as gender or limb problems. As for the individual differences, teacher data in which a behavior of the care-receiver and a waveform are associated is generated and then pattern detection is performed. Further, as for the detection value data, because individual differences occur among the beds 601 and individual differences occur among the care-receivers, a learning method and teacher data that are appropriate for each individual are prepared. Accordingly, it is possible to detect a get-out-of-bed timing from the waveform with high accuracy.

Subsequently, the threshold processing unit 503 performs the threshold processing on the GOB probability map that is obtained by the GOB probability map calculation unit 510 (Step S24). Specifically, the threshold processing unit 503 determines whether the GOB probability is higher than those at other times by using the threshold, on the basis of the GOB probability map that is obtained by the GOB probability map calculation unit 510. In normal use, it is preferable to calculate a base line during a sleeping period in which getting out of bed does not occur. It is determined, in advance, a degree of increase in the GOB probability with respect to the base line as a time that serves as the threshold. Further, oscillation due to roll-over may result in a waveform that is similar to a waveform generated by getting out of bed. It is important to accumulate the data as described above. In particular, load states on the four legs of the bed 601 vary between the roll-over and the getting out of bed. In the case of getting out of bed, bias occurs in one surface in which a load center is present (a side surface of the bed 601 from which the care-receiver gets out of bed and takes a step forward). In the case of roll-over, a waveform in which a load is moved in a direction of the roll-over from the center of the bed 601 is obtained. In this manner, accumulation of data by machine learning is meaningful for observation of a load balance among the four load sensors 602.

Therefore, the GOB probability map calculation unit 510 calculates a total GOB probability based on the balance among the four load sensors 602, and at the same time, calculates a GOB probability of each of the four load sensors 602.

Subsequently, the sensor selection unit 5051 compares GOB scores and selects the load sensors 602 (Step S25). The sensor selection unit 5051 changes the load sensors 602 to be selected on an as-need basis while monitoring the scores. Then, the sensor selection unit 5051 selects the three load sensors 602 from among the four load sensors 602 that are currently used. The purpose and the effect of the selection will be described below.

As described above, the load sensors 602 are installed in the four legs of the bed 601. The four legs are adjusted such that a load is equally applied, but the load is applied to three of the four legs at the time of getting out of bed. In general, this is a phenomenon in which a balance is kept at three points, and a remaining single point slightly floats and the load is not applied to the single point. Further, at the time of getting out of bed, a position of the center of gravity of the subject varies depending on a position and a side at which the subject stands up when getting out of the bed, and therefore, three points to be used to support the load are indefinite. The load sensors 602 are not able to accurately determine and detect getting out of bed unless certain loads are applied, and therefore, only the three load sensors 602 are able to accurately detect waveforms indicating the getting out of bed. As for the single load sensor 602 to which the load is not applied, the waveform indicating the getting out of bed is disturbed, which leads to noise and reduction in determination accuracy. In other words, by determining the waveforms and selecting the load sensors 602, it is possible to detect waveforms with high accuracy and detect a get-out-of-bed timing with high accuracy.

Subsequently, the waveform synthesis unit 5052 synthesizes the waveforms of the three load sensors 602 that are selected by the sensor selection unit 5051 (Step S26). If only the single load sensor 602 of the bed 601 is used, a change is likely to occur due to an external cause or the like. Further, with use of only the single load sensor 602, in some cases, it may be difficult to distinguish between roll-over and getting out of bed. Therefore, the waveform synthesis unit 5052 synthesizes the waveforms of the load sensors 602 at the three positions, so that it is possible to easily detect the waveforms.

Due to the waveform synthesis performed by the waveform synthesis unit 5052, it is possible to further remove various kinds of noise, so that it is possible to improve detection accuracy of the getting-out-of-bed timing. The noise includes oscillation, such as oscillation of a refrigerator or oscillation due to a fan of a personal computer (PC), which is irregularly applied to only the certain single load sensor 602. It is possible to reduce an influence of the noise as described above by waveform synthesis performed by the waveform synthesis unit 5052.

The peak detection unit 505 performs final determination on whether getting out of bed has occurred, on the basis of amplitude of the peak in the synthesized waveform obtained by the waveform synthesis unit 5052 (Step S27).

If the peak detection unit 505 does not detect the peak (No at Step S27), the process returns to a loop for data acquisition again (Step S21). Repeating the loop about every 5 seconds (sec) is satisfactory for detection of getting out of bed, and if the speed of repetition is increased, a speed of handling by the care-giver is increased. A waveform in an appropriate time interval is needed for waveform analysis, and therefore, a loop of about 500 msec is appropriate at the fastest.

If the peak detection unit 505 detects the peak (Yes at Step S27), the peak detection unit 505 issues a getting-out-of-bed alarm (Step S28). As for the getting-out-of-alarm, information is transmitted to the terminal 610 that is carried by the care-giver. In response to the alarm, the care-giver visits a room of the care-receiver and assists the care-receiver to move to a wheelchair or go to the bathroom.

In general, the bed sensor system 600 is always activated while the care-receiver is present. As for the bed sensor system 600, if the care-receiver leaves the facility for example (Yes at Step S29), the bed sensor system 600 is terminated.

In the first modification, the sensor is selected based on the waveform data. In other words, it is possible to eliminate a sensor that has large noise or in which a signal does not appear. As the sensor that needs to be eliminated as described above, in some cases, the single load sensor 602 to which the load is not applied among the four load sensors 602 that are arranged on the four legs of the bed 601 as described in the first modification may have large noise and is less likely to have an event waveform, for example. The synthesized waveform of the load sensors 602 as described above has reduced noise and automatic detection accuracy is improved. By performing automatic detection with high accuracy, it is possible to provide a detection result by, as in the interface as illustrated in FIG. 10, outputting buzzer sound or providing a display marker with high visibility. This not only simply improves the visibility of the waveform, but also improves accuracy and ease of determination by attracting attention of a user In each of the embodiments as described above, when at least one of the functional units of the biological signal measurement system 1 is implemented by executing a program, the program is provided by being incorporated in a ROM or the like in advance. Further, the program executed by the biological signal measurement system 1 according to the embodiments as described above may be provided by being recorded in a computer readable recording medium, such as a compact disc-ROM (CD-ROM), a flexible disk (FD), a CD-recordable (CD-R), or a digital versatile disk (DVD), in a computer-installable or computer-executable file format.

Furthermore, the program executed by the biological signal measurement system 1 of each of the embodiments as described above may be stored in a computer connected to a network, such as the Internet, and may be provided by download via the network.

Moreover, the program executed by the biological signal measurement system 1 of each of the embodiments as described above may be provided or distributed via a network, such as the Internet. Furthermore, the program executed by the biological signal measurement system 1 of each of the embodiments as described above has a module structure that includes at least any of the functional units as described above, and as actual hardware, each of the functional units as described above is loaded and generated on a main storage device by causing a CPU to read the program from a ROM or the like and execute the program.

According to an embodiment, it is possible to determine a single peak from among candidate peaks of waveforms that are extracted from time series of a plurality of sensors, to determine a reference point for analysis.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

The method steps, processes, or operations described herein are not to be construed as necessarily requiring their performance in the particular order discussed or illustrated, unless specifically identified as an order of performance or clearly identified through the context. It is also to be understood that additional or alternative steps may be employed.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. An information processing apparatus comprising:
circuitry configured to:
   extract, by predetermined pattern matching, candidate peaks in a certain arbitrary period of time from among a plurality of pieces of waveform data;
   determine, from among the candidate peaks of the waveform data, a single peak based on a score related to the pattern matching;
   determine a match rate for a health condition based on the waveform data; and
   output display information for displaying a position of the peak, the display information includes the match rate for the health condition based on the waveform data; and
a display configured to display the display information, wherein the circuitry is further configured to:
   generate synthesized wave data by synthesizing pieces of waveform data in a same time interval of the extracted waveform data;
   receive measurement data from a measurement apparatus, the measurement data including:
      electroencephalography signals from an electrode of the measurement apparatus; and
      magnetoencephalography signals from a magnetic sensor of the measurement apparatus,
   add a weight to at least one of the electrode and the magnetic sensor based on the determined match rate, and
wherein the waveform data includes the measurement data.

2. The information processing apparatus according to claim 1, wherein the waveform data includes position information of at least one epilepsy legion, and
wherein the position information is to be used for performing an epilepsy operation.

3. A non-transitory computer-readable medium including programmed instructions that cause a computer to
   extract, by predetermined pattern matching, candidate peaks in a certain arbitrary period of time from among a plurality of pieces of waveform data;
   determine, from among the candidate peaks of the waveform data, a single peak based on a score related to the pattern matching;
   determine a match rate for a health condition based on the waveform data;

output display information, to a display, for displaying a position of the peak and the match rate for the health condition based on the waveform data;

generate synthesized wave data by synthesizing pieces of waveform data in a same time interval of the extracted waveform data extracted;

receive measurement data from a measurement apparatus, the measurement data including:
- electroencephalography signals from an electrode of the measurement apparatus, and
- magnetoencephalography signals from a magnetic sensor of the measurement apparatus; and add a weight to at least one of the electrode and the magnetic sensor based on the determined match rate, wherein the waveform data includes the measurement data.

4. The computer-readable medium according to claim 3, wherein the waveform data includes position information of at least one epilepsy legion, and
  wherein the position information is to be used for performing an epilepsy operation.

5. An information processing method for controlling an information processing apparatus, the information processing method comprising:
  extracting, by predetermined pattern matching, candidate peaks in a certain arbitrary period of time from among a plurality of pieces of waveform data;
  determining, from among the candidate peaks of the waveform data, a single peak based on a score related to the pattern matching;
  determine a match rate for a health condition based on the waveform data; and
  outputting display information for displaying a position of the peak, the display information includes the match rate for the health condition based on the waveform data;
  displaying the display information;
  generating synthesized wave data by synthesizing pieces of waveform data in a same time interval of the extracted waveform data;
  receiving measurement data from a measurement apparatus, the measurement data including:
    electroencephalography signals from an electrode of the measurement apparatus, and
    magnetoencephalography signals from a magnetic sensor of the measurement apparatus; and
  adding a weight to at least one of the electrode and the magnetic sensor based on the determined match rate,
  wherein the waveform data includes the measurement data.

6. The information processing method according to claim 5, wherein the waveform data includes position information of at least one epilepsy legion, and
  wherein the position information is to be used for performing an epilepsy operation.

* * * * *